US011478665B2

(12) United States Patent
Snider, III et al.

(10) Patent No.: US 11,478,665 B2
(45) Date of Patent: Oct. 25, 2022

(54) TECHNIQUES FOR SPATIALLY FRACTIONATED PARTICLE BEAM THERAPY

(71) Applicant: University Of Maryland, Baltimore, Baltimore, MD (US)

(72) Inventors: James William Snider, III, Baltimore, MD (US); William F. Regine, Cockeysville, MD (US); Mingyao Zhu, Ellicott City, MD (US); Katja Langen, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 439 days.

(21) Appl. No.: 16/486,075

(22) PCT Filed: Feb. 15, 2018

(86) PCT No.: PCT/US2018/018323
§ 371 (c)(1),
(2) Date: Aug. 14, 2019

(87) PCT Pub. No.: WO2018/152302
PCT Pub. Date: Aug. 23, 2018

(65) Prior Publication Data
US 2020/0001118 A1  Jan. 2, 2020

Related U.S. Application Data

(60) Provisional application No. 62/459,120, filed on Feb. 15, 2017.

(51) Int. Cl.
*A61N 5/10* (2006.01)

(52) U.S. Cl.
CPC ......... *A61N 5/1081* (2013.01); *A61N 5/1031* (2013.01); *A61N 5/1047* (2013.01); *A61N 5/1079* (2013.01); *A61N 2005/1087* (2013.01)

(58) Field of Classification Search
CPC ......... A61N 5/1079; A61N 2005/1087; A61N 5/103; A61N 5/1047; A61N 5/1031; A61N 5/1042; A61N 5/1081
See application file for complete search history.

(56) References Cited

U.S. PATENT DOCUMENTS 7,834,336 B2 * 11/2010 Boeh .................... A61N 5/1042
250/505.1
8,395,131 B2    3/2013 Wu
(Continued)

OTHER PUBLICATIONS

Buchsbaum, Proton therapy—What is it and what can it do to help my patients?, Appl Rad Oncol, 2013, pp. 6-15, vol. 2.
(Continued)

*Primary Examiner* — Christine H Matthews
*Assistant Examiner* — Joshua Daryl D Lannu
(74) *Attorney, Agent, or Firm* — Wolter Van Dyke Davis, PLLC; Eugene Molinelli; Cian O'Brien

(57) ABSTRACT

Techniques for particle beam therapy include receiving a target region inside a subject for particle therapy, a minimum dose inside the target region, and a maximum dose inside the subject but outside target region. Multiple beam axis angles are determined, each involving a gantry angle and a couch position. Multiple spots within the target region are determined. For each beam axis angle a pristine particle scan beam (not coaxial with any other particle scan beam) is determined such that a Bragg Peak is directed to a spot, and repeated until every spot is subjected to a Bragg Peak or an intersection of two or more such pristine scan beams. Output data indicating the pristine beamlets is stored for operation of a particle beam therapy apparatus.

20 Claims, 21 Drawing Sheets

(56) References Cited

U.S. PATENT DOCUMENTS

2012/0136194 A1* 5/2012 Zhang .................. A61N 5/103
600/1
2016/0287908 A1 10/2016 Bennett et al.

OTHER PUBLICATIONS

Gao, et al., Spatially Fractionated (GRID) Radiation Therapy Using Proton Pencil Beam Scanning (PBS): A Feasibility Study (abstract), Int J Radiat Biol Phys, 2015, pp. SE562, vol. 93.

Garcia-Barros, et al., Tumor response to radiotherapy regulated by endothelial cell apoptosis, Science, 2003, pp. 1155-1159, vol. 300.

Griffin, et al., Microbeam radiation therapy alters vascular architecture and tumor oxygenation and is enhanced by a galectin-1 targeted anti-angiogenic peptide, Radiat Res, 2012, pp. 804-812, vol. 177.

Guan, et al., Spatial mapping of the biologic effectiveness of scanned particle beams: towards biologically optimized particle therapy, Sci Rep, 2015, pp. 1-10, vol. 5:9850.

Haimovitz-Friedman, et al., Ionizing radiation acts on cellular membranes to generate ceramide and initiate apoptosis, J Exp Med, 1994, pp. 525-535, vol. 180.

Haimovitz-Friedman, et al., Protein kinase C mediates basic fibroblast growth factor protection of endothelial cells against radiation-induced apoptosis, Cancer Res, 1994, pp. 2591-2597, vol. 54.

Henry, et al., Proton Grid Therapy: A Proof-of-Concept Study, Technol Cancer Res Treat, 2016, pp. 749-757, vol. 16.

Huhn, et al., Spatially fractionated GRID radiation treatment of advanced neck disease associated with head and neck cancer, Technol Cancer Res Treat, 2006, pp. 607-612, vol. 5.

Kavanagh, et al., Stereotactic radiosurgery and stereotactic body radiation therapy: an overview of technical considerations and clinical applications, Hematol Oncol Clin North Am, 2006, pp. 87-95, vol. 20.

Lin, et al., Ceramide mediates radiation-induced death of endothelium, Crit Care Med, 2000, pp. N87-93, vol. 28.

McMahon, et al., A kinetic-based model of radiation-induced intercellular signaling, PLoS One, 2013, p. e54526, vol. 8.

Meyer, et al., Stereotactic ablative radiotherapy in the framework of classical radiobiology: response to Drs. Brown, Diehn, and Loo, Int J Radiat Oncol Biol Phys, 2011, pp. 1599-1600, vol. 79.

Mohiuddin, et al., Spatially fractionated (GRID) radiation for palliative treatment of advanced cancer, Radia Oncol Invest, 1996, pp. 41-47, vol. 4.

Mohiuddin, et al., High-dose spatially fractionated radiation (Grid): A new paradigm in the management of advanced cancer, Int J Radiat Oncol Biol Phys, 1999, pp. 721-727, vol. 45.

Prasanna, et al., Exploiting sensitization windows of opportunity in hyper and hypofractionated radiation therapy, J Thorac Dis, 2014, pp. 287-302, vol. 6.

Santana, et al., Acid sphingomyelinase deficient human lymphoblasts and mice are defective in radiation-induced apoptosis, Cell, 1996, pp. 189-199, vol. 86.

Sathishkumar, et al., The impact of TNF-alpha induction on therapeutic efficacy following high dose spatially fractionated (GRID) radiation, Technol Cancer Res Treat, 2002, pp. 141-147, vol. 1.

Shareef, et al., Role of tumor necrosis factor alpha and TRAIL in high-dose radiation-induced bystander signaling in lung adenocarcinoma, Cancer Res, 2007, pp. 11811-11820, vol. 67.

Sathishkumar, et al., Elevated sphingomyelinase activity and ceramide concentralion in serum of patients undergoing high dose spatially fractionated radiation treatment: implications for endothelial apoptosis, Cancer Biol Ther, 2005, pp. 979-986, vol. 4.

Snider, et al., Use of "Virtual" High-Dose-Rate (HDR) Brachytherapy via Spatially Fractionated GRID Radiation Therapy (SFGRT) as Part of Neoadjuvant Therapy in Poor Prognosis, Bulky Sarcomas, Int J Radiat Oncol Biol Phys, 2014, p. S767, vol. 90(1).

Snider, et al., A Novel Method for the Delivery of 3-Dimensional High-Dose Spatially Fractionated Radiation Therapy With Pencil Beam Scanning Proton Therapy: Maximizing the Benefit of the Bragg Peak (abstract), Int J Radiat Oncol Biol Phys, 2017, pp. S232-S233, vol. 99(2).

Videtic, et al., A Randomized Phase 2 Study Comparing 2 Stereotactic Body Radiation Therapy Schedules for Medically Inoperable Patients With Stage I Peripheral Non-Small Cell Lung Cancer: NRG Oncology RTOG 0915 (NCCTG N0927), Int J Radiat Oncol Biol Phys, 2015, pp. 757-764, vol. 93(4).

Welsh, et al., Phase 2 5-Arm Trial of Ipilimumab Plus Lung or Liver Stereotactic Radiation for Patients with Advanced Malignancies (abstract), Int J Radiat Oncol Biol Phys, 2017, p. 1315, vol. 99(5).

Wilson, Radiological use of fast protons, Radiology, 2016, pp. 487-491, vol. 47.

Wu, et al., On Modern Technical Approaches of Three-Dimesional High-Dose Lattice Radiotherapy (LRT), Cureus, p. e9, vol. 2(3).

Zhang, et al., Spatially fractionated radiotherapy (GRID) using helical tomotherapy, J Appl Clin Med Phys, 2016, pp. 396-407, vol. 17(1).

Khan, et al., Khan's the Physics of Radiation Therapy: Lippincott Williams & Wilkins, book, 2014, pp. 454-474.

International Search Report and Written Opinion for International Patent Application No. PCT/US18/18323 dated May 16, 2018, pp. 1-9.

* cited by examiner

TECHNIQUES FOR SPATIALLY FRACTIONATED PARTICLE BEAM THERAPY

CROSS-REFERENCE TO RELATED APPLICATIONS

This application is a 371 national stage application of PCT Application No. PCT/US18/18323, filed Feb. 15, 2018, and claims benefit of Provisional Appln. 62/459,120 filed Feb. 15, 2017, the entire contents of which are hereby incorporated by reference as if fully set forth herein, under 35 U.S.C. § 119(e).

BACKGROUND

The use of proton and other particle beam therapy for treating cancer has greatly increased over the past decade, mostly because of the advantageous properties of such particle beams. A particle beam initially deposits a relatively low dose upon entering the patient, and the deposited dose rises to a sharp maximum, known as the Bragg peak, near the end of the beam's range in the patient. The range in the patient is a function of the initial energy of the particles, with greater energy producing a Bragg Peak at greater depths. The sharp Bragg Peak and the finite range of the beam provide the ability to deliver a highly conformal treatment, allowing for dose escalation to the tumor and/or a reduction of exposure to the surrounding healthy tissues. However, errors in patient setup or positioning, day-to-day variations in internal anatomy, anatomical motion, changes to tumor and normal tissue in response to treatment, and other biological factors all lead to uncertainties in accurate delivery of particle therapy. Because of these uncertainties, standard proton treatment planning techniques generally include the use of treatment volume expansions to ensure target coverage or robust evaluation or both. These large safety margins also limit the ability to exploit the steep dose gradients at the distal edge of the Bragg peak, potentially reducing the full clinical potential of proton radiation therapy.

Whether employed with proton therapy, carbon ion therapy, helium ion therapy, etc., this modality provides impressive dose delivery and distribution advantages based on the limited range of dose deposition of the beam. In other words, the Bragg Peak provides low entrance dose with virtually no exit dose. This has permitted improved normal tissue sparing and, sometimes, allowed for dose-escalation to tumors even deep within the body. Results thus far are quite promising.

Some of the advantages of the Bragg Peak distribution are reduced or lost, however, as particle beams of varying energy targeting different depths in the subject are delivered along the same beam angle. Because the Bragg Peak of dose delivery is rather limited in depth many energy layers of varying initial particle energy are used along a particular beam path direction to produce a spread out Bragg Peak (SOBP). Doses accumulate on the proximal side of the successive Bragg Peaks, thus exposing tissue outside and proximal to the target region to an accumulated dose that can approach a full dose of the prescribed SOBP dose, depending on target depth. As used herein, a target region is a one dimensional (1D) or two dimensional (2D) or three dimensional (3D) portion of a subject that is to be irradiated for the purpose of killing cells that intersect the target region.

In previous radiation therapy (radiotherapy) approaches using orthovoltage, cobolt and other high energy photons, rather than particles like protons with a rest mass, it was discovered that efficacious treatment resulted even with non-uniform delivery of radiation throughout the target region. This proved especially beneficial in deep seated, large tumors treated with lower energy beams (e.g. orthovoltage) when skin toxicity was particularly severe. Spatially fractionated radiotherapy (GRID) is an external beam radiotherapy technique utilized today primarily as a method for dose-escalation in large, bulky tumors. Historically, this has been employed to deliver radiation to deep-seated tumors with low energy radiation beams while geographically sparing superficial tissues between small delivered beamlets of radiation. In recent, years, these beamlets have been delivered with megavoltage linear accelerators to effect "streaks" or peaks of high dose within the target region coupled with valleys inside the target region between beamlets. This has been achieved through several methods including cerrobend block based "GRIDs" or multileaf collimator (MLC) designed apertures. With the modernization of radiation therapy equipment and techniques the idea and execution of 3-dimensional (3D) LATTICE radiotherapy has been described and delivered. This approach employs intensity modulated radiation therapy (IMRT) to deliver the peaks associated with GRID therapy as 3-dimensional islands within the target tumor while providing a more homogeneous dose across the remainder of the target region between peaks.

SUMMARY

While it has been proposed that LATTICE or GRID radiation could be delivered with particle therapy, none of the current efforts take full advantage of the properties of particle therapy, and therefore fall short of optimal implementation. Applicants have developed techniques described here that more efficaciously combine the benefits of GRID and LATTICE radiotherapy with the unique benefits of particle therapy. These techniques are collectively referenced herein as Particle GRID techniques, and eschew the generation of SOBPs. In some embodiments, the Particle GRID techniques take advantage of the same bystander effects of GRID radiotherapy or a direct tumor ablative effect, or both. In some embodiments, the Particle GRID techniques also take advantage of a sparing effect. When beamlets of high dose are far enough apart, regions of proximal normal tissue that are partially irradiated but spared from high doses not only heal better but also heal into the higher dose regions within the beamlets. The distance associated with this healing effect is called a sparing distance hereinafter. In contrast, peaks of high dose per fraction within the tumor are expected to produce ablative effects within the high dose region and the "bystander" effect in nearby tumor tissue, causing greater than expected (by dose) tumoral cell kill effect in surrounding tumor. The immunostimulatory nature of high dose per fraction radiotherapy has been well described and may be another cause of better tumor cell kill both within the target region and elsewhere in the subject. The pairing of the Particle GRID techniques with immunotherapy or immune checkpoint inhibitors or both is included in some embodiments.

In a first set of embodiments, a method implemented on a processor includes receiving first data indicating a target region inside a subject for particle therapy, a minimum dose inside the target region, and a maximum dose inside the subject but outside the target region. The method also includes determining multiple beam axis angles, each beam axis angle comprising a gantry angle and a couch position. The method further includes determining multiple spots within the target region. Yet further, the method includes determining for each beam axis angle one or more pristine beamlets, each with corresponding scan beam angle and particle initial energy to direct a Bragg Peak at a spot of the multiple spots; and, repeating until every spot of the multiple spots is subjected to a Bragg peak or an intersection of two or more pristine beamlets. The method even further includes causing output data indicating the pristine beamlets to be stored for operation of a particle beam therapy apparatus. In some embodiments, the method includes operating the particle beam therapy apparatus.

In some embodiments of the first set, the method yet further includes determining a spatial distribution of delivered dose inside the subject accumulated from all of the multiple beamlets; and, determining whether the spatial distribution of delivered dose satisfies the first data. Only if it is determined that the spatial distribution of delivered dose satisfies the first data, is the output data caused to be stored for operation of the particle beam therapy apparatus.

In some embodiments of the first set, the spots are based at least in part on a target spacing distance for a type of tissue in the target region. For example, in some embodiments, the spots are spaced apart from each other by about twice the target spacing distance. As another example, in some embodiments, spots are spaced apart from an edge of the target region by about the target spacing distance. In some embodiments the target spacing distance is about 0.3 to about 1 centimeter. In some embodiments, the spots are spaced apart from each other by about 1.5 to 3 cm to achieve a peak-to-valley dose ratio (target distance) on the order of 4:1 to 8:1.

In some embodiments of the first set, no two scan beams for one beam axis angle are closer inside the subject but outside the target region than a scan separation distance based at least in part on a sparing distance. In some of these embodiments scan separation distance is about twice the sparing distance. In some embodiments, the sparing distance is about 1.5 centimeter to about 3 centimeters.

In some embodiments of the first set, the multiple spots within the target region are determined such that no two spots are coaxial in a beam's eye view along any of the multiple beam axis angles. In some of these embodiments, a pristine beamlet is determined for every spot separated by at least the sparing distance in a beam's eye view for the beam axis angle. In some of these embodiments, the multiple spots is a grid of spots separated by a distance based at least in part on the target spacing distance, and the grid is rotated such that each spot is separated in the beam's eye view for the beam axis angle.

In some embodiments of the first set, the multiple spots within the target region is a grid of spots rotated such that each spot is separated in the beam's eye view for the beam axis angle by at least the sparing distance. In some of these embodiments, a pristine beamlet is determined for every spot in a beam's eye view for the beam axis angle.

In some embodiments of the first set, a portion inside the target region of the spatial distribution of delivered dose is heterogeneous with a maximum and minimum in delivered dose which differ by about a factor of about four. In some of these embodiments, the minimum dose inside the target region is about 4 gray (Gy) relative biological effectiveness adjusted (RBE). In some of these embodiments, the peak dose ranges from about 10 Gy RBE to about 20 Gy RBE and the valleys from about 1 Gy RBE to about 6 Gy RBE. In some of these embodiments, the spot distribution is overlaid onto a traditional, SOBP, homogenous target dose of about 2 Gy RBE to create a simultaneous integrated boost technique (SIB).

In other sets of embodiments, a computer-readable medium or system is configured to perform one or more steps of one or more of the above methods.

Still other aspects, features, and advantages are readily apparent from the following detailed description, simply by illustrating a number of particular embodiments and implementations, including the best mode contemplated for carrying out the invention. Other embodiments are also capable of other and different features and advantages, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

Embodiments are illustrated by way of example, and not by way of limitation, in the figures of the accompanying drawings in which like reference numerals refer to similar elements and in which.

DETAILED DESCRIPTION

A method and apparatus are described for delivering spatially fractionated particle beam therapy In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements at the time of this writing. Furthermore, unless otherwise clear from the context, a numerical value presented herein has an implied precision given by the least significant digit. Thus a value 1.1 implies a value from 1.05 to 1.15. The term "about" is used to indicate a broader range centered on the given value, and unless otherwise clear from the context implies a broader range around the least significant digit, such as "about 1.1" implies a range from 1.0 to 1.2. If the least significant digit is unclear, then the term "about" implies a factor of two, e.g., "about X" implies a value in the range from 0.5X to 2X, for example, about 100 implies a value in a range from 50 to 200. Moreover, all ranges disclosed herein are to be understood to encompass any and all sub-ranges subsumed therein. For example, a range of "less than 10" for a positive valued parameter can include any and all sub-ranges between (and including) the minimum value of zero and the maximum value of 10, that is, any and all sub-ranges having a minimum value of equal to or greater than zero and a maximum value of equal to or less than 10, e.g., 1 to 4.

Some embodiments of the invention are described below in the context of proton therapy to human patients as subjects. However, the invention is not limited to this context. In other embodiments, other high energy radiation, including Carbon ions, Helium ions (including helium nuclei called alpha particles), electrons (called beta particles), positrons (called beta plus particles), and X-rays photons, are used on non human living, non-living or other inanimate subjects.

1. OVERVIEW OF HARDWARE COMPONENTS

Figure 1A:
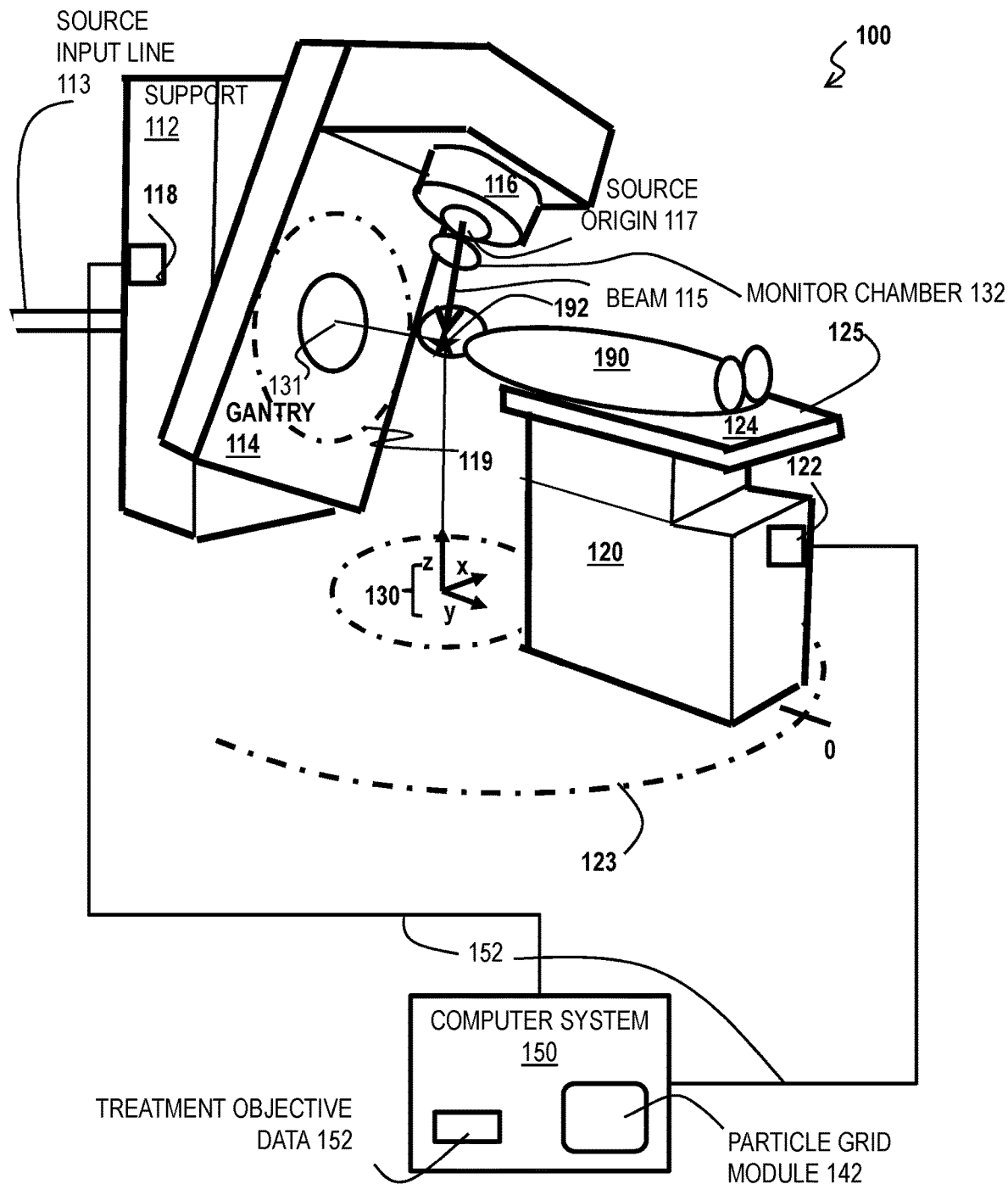
FIG. 1A is a block diagram that illustrates an example system for irradiation, according to an embodiment.

FIG. 1A is a block diagram that illustrates an example system 100 for irradiation, according to an embodiment. For purposes of illustration, a living subject 190 is depicted, but is not part of the system 100. As illustrated in FIG. 1A, a target region 192 is positioned within the subject 190. In an example embodiment, the target region 192 includes tumor cells. The system 100 includes a gantry 114 mounted to rotate around a support structure 112 and a moveable couch 124 mounted on couch support 120. The system also includes a radiation source output port 116 at position 117, called a source origin, which emits a beam 115 that penetrates to the target area 192. In some embodiments, the radiation is generated in a separate accelerator (e.g., a cyclotron or synchrotron) and fed into the gantry 114 along source input line 113 through a gantry support structure 112 and directed by one or more steering magnets in support 112 or gantry 114 or some combination to output port 116. In some embodiments, scanning magnets are included at the output port 116. In various embodiments other beam modifying devices are used, such as magnets, collimators, multi-leaf collimators, apertures, range-shifters/preabsorbers, compensators, etc. Hereinafter the radiation source will be understood to mean the output port 116 unless otherwise clear from the context. Combining the effects of multiple beams (their initial energies, intensities and shapes), the goal is to transmit high dose to the target region 192, and low dose to the tissue of the subject 190 outside the target region. During the operation of the system 100, the radiation source output port 116 rotates with gantry 114 around the support structure 112 and the subject 190 is positioned on a moveable couch 124 mounted on couch support 120, so that the beam is directed at the target region 192 from multiple directions.

In the stationary global spatial coordinate system 130, the vertical dimension is indicated by a z axis, and the horizontal dimensions by an x axis transverse to the couch at a zero couch angle and a y axis oriented along the couch at zero couch angle as shown in FIG. 1A. At 0 couch angle with a patient on his or her back as the subject, planes through the subject parallel to the x-y plane provides coronal slices, planes parallel to the y-z plane provide sagittal slices, and planes parallel to the x-z plane provide transverse slices of the patient (the latter sometimes called axial slices, but that term is avoided herein to avoid confusion with an axial direction, as used herein, which forms an axis of a beam or beamlet emitted from the source 116). The coordinate system 130 is related to the Digital Imaging and Communications in Medicine (DICOM) standard axes as given by Equation 1a through 1c.

$$X_{global} = X_{DICOM} \tag{1a}$$

$$Y_{global} = -Z_{DICOM} \tag{1b}$$

$$Z_{global} = -Y_{DICOM} \tag{1c}$$

The gantry rotates an angle θ 119 in the x-z plane about an axis of rotation considered to occur at the origin 131 of the z axis and parallel to the y axis. In various embodiments, the couch 124 can be moved with up to 6 degrees of freedom, including 3 displacements (x, y, z directions) and 3 angles (pitch, roll, yaw). For example, the couch can be rotated an angle φ 123 in the x-y plane around the z axis or displaced in the y direction relative to the base 120 at a couch angle of zero, or some combination.

As illustrated in FIG. 1A, a computer system 150 is provided to determine the initial particle energy, intensity and shape of the beam 115 from the source output port 116 for each of multiple beams at one or more gantry angles and one or more couch angles and one or more couch heights or displacements according to a treatment plan. The computer system 150 also transmits the appropriate parts of the determined information: to a controller 118 for the gantry and radiation source; and to a controller 122 for couch 124. The information is transmitted over one or more wired or wireless communication lines 152.

The computer system 150 includes a Particle GRID module 142 to determine a spatially fractionated particle therapy treatment plan, according to one or more of the techniques described herein.

Figure 11:
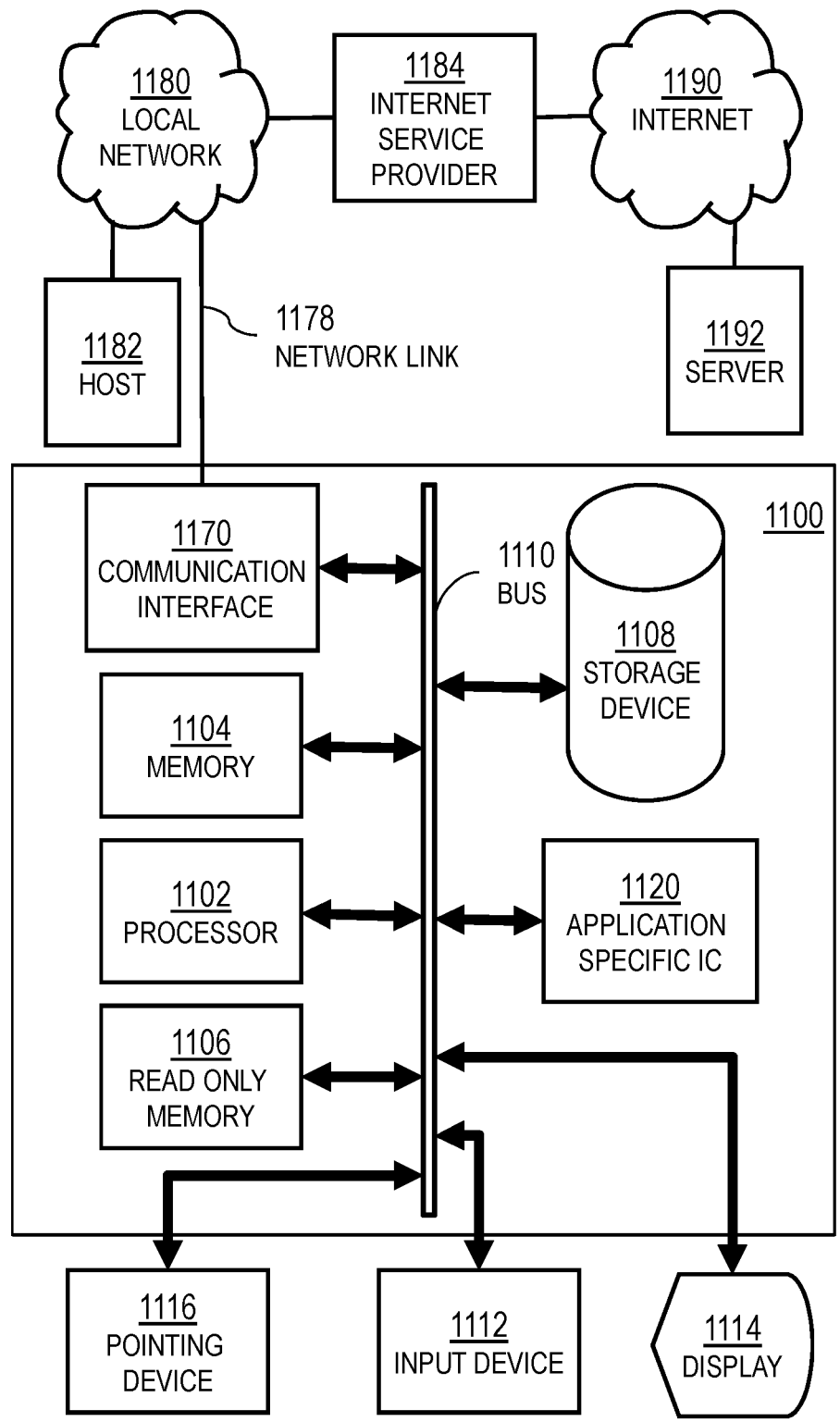
FIG. 11 is a block diagram that illustrates a computer system upon which an embodiment of the invention may be implemented.
Figure 12:
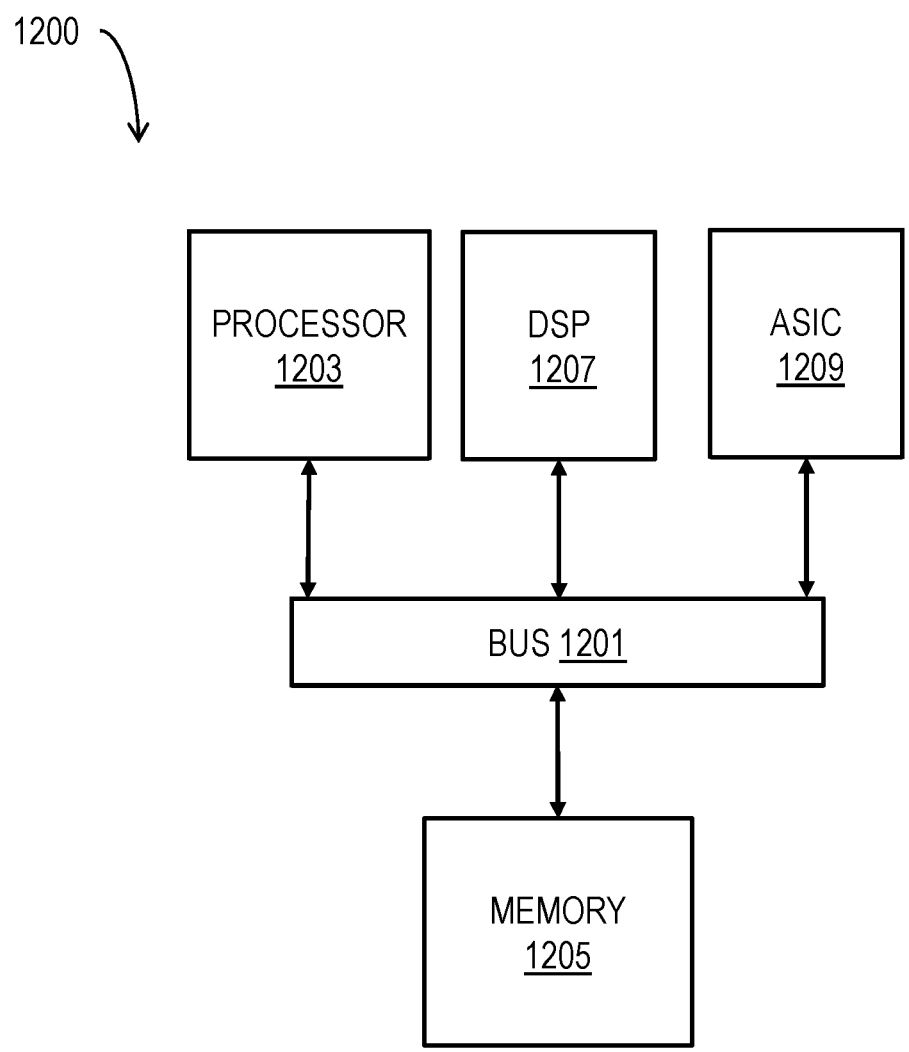
FIG. 12 illustrates a chip set upon which an embodiment of the invention may be implemented.

In various embodiments, the computer system 150 comprises one or more general purpose computer systems, as depicted in FIG. 11 or one or more chip sets as depicted in FIG. 12, and instructions to cause the computer or chip set to perform one or more steps of a method described below with reference to FIG. 7A.

Although processes, equipment, and structures are depicted in FIG. 1A as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. For example all or part of module 142 may be performed by controller 118 for the gantry and radiation source or by controller 122 for the couch 120, or some combination.

A treatment objective is prepared for treating a subject, such as a human or animal patient or a surrogate such as an inanimate phantom or control object, and includes treatment objective data 152 that indicates information about the subject placement on the couch 124, the height and orientation angle φ of the couch, the outer surface of the subject at φ=0 in global coordinates, the target region in global coordinates, including an outer surface of the target region and a central point, called the isocenter. The isocenter is near or inside the target region 192; and, is aligned with the axis of rotation of the gantry and the axis of rotation of the couch. After treatment of at least a portion of the target region 192 in the neighborhood of the isocenter, the couch can be moved horizontally and vertically or the gantry rotated, or some combination, to produce a different beam axis angle so that a different portion of the target region inside the subject can be treated and a different point occupies the isocenter. As used herein, a "beam axis angle" refers to a particular configuration of gantry angle, couch height, couch horizontal displacement and couch angle. Typically, successive beam axis angles occur at the same couch height, horizontal displacement and couch angle but at successive different gantry angles.

Figure 1B:
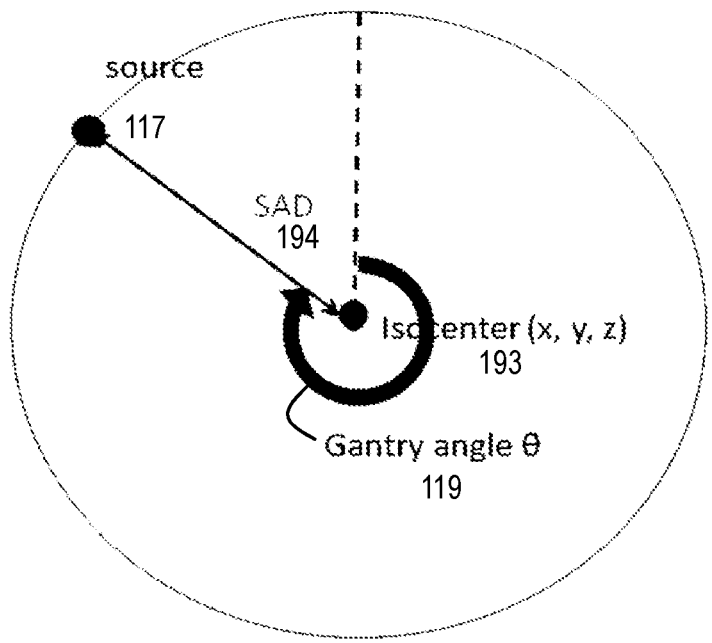
FIG. 1B and FIG. 1C are block diagrams that illustrate example gantry and couch angles, respectively, manipulated according to an embodiment.
Figure 1C:
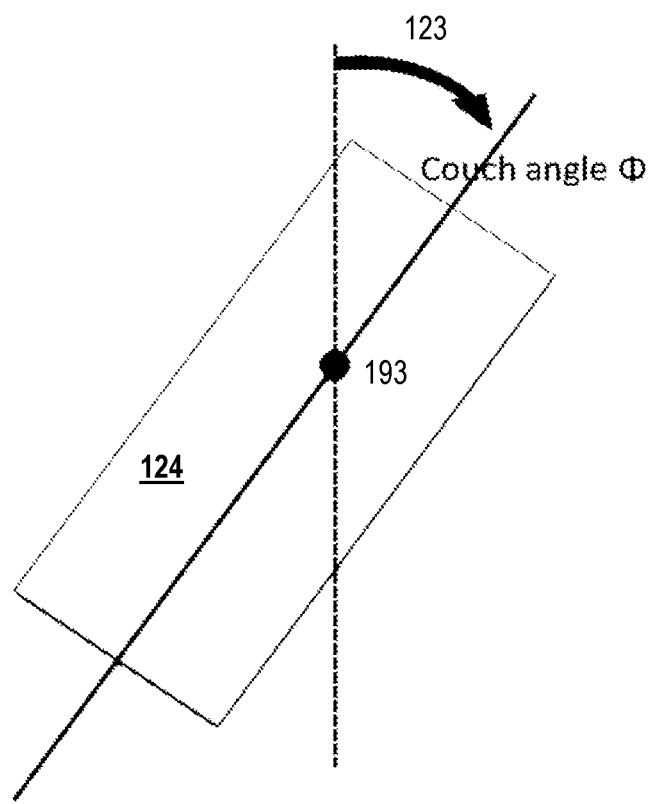

FIG. 1B and FIG. 1C are block diagrams that illustrate example gantry and couch angles, respectively, manipulated according to an embodiment. FIG. 1B depicts the gantry angle θ, measured in this example clockwise relative to the radiation source pointing straight down (−z direction) in the z-x plane looking back along the −y direction. FIG. 1C depicts the horizontal surface of the couch 124 in the x-y plane and the couch angle φ, measured in this example clockwise, looking in the −z direction, from the y axis that is parallel to the axis of rotation of the gantry.

Figure 1D:
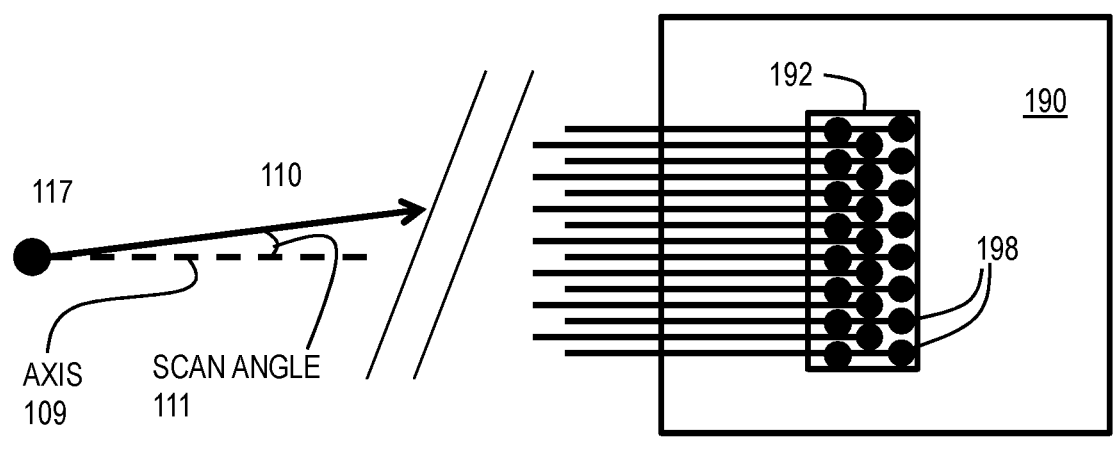
FIG. 1D is a block diagram that illustrates an example scanning pencil beam radiation source, used in many modern particle beam sources, according to some embodiments.

FIG. 1D is a block diagram that illustrates an example scanning pencil beam radiation source, used in many modern particle beam sources, according to some embodiments. At any instant, only a thin beam called a pencil beam (also called a beamlet) is emitted from a source output port 117. Scanning components (e.g., magnets or optics, not shown) are used to point the pencil beam through any of a variety of small scan angles 111 around a beam axis 109 at the center of a fan of such beamlets. The scanning is accomplished over a short time, completing the fan in a time on the order of milliseconds to seconds. Each beam 110 penetrates the skin of a subject 190 to a target region 192 where the energy is largely absorbed at one subregion 198 called a target volume, also called a "spot" hereinafter for convenience. As the pencil beam is scanned over multiple angles 111, the energy is primarily absorbed at multiple target volumes 198 at one depth within the subject. By using a pencil beam of different initial particle energy, the beam energy is absorbed in a target volume at a different depth. In a short time, multiple target volumes that span the entire target region 192 are radiated. For example, in some experimental embodiments, the distance from the output port is about 230 cm, beamlet width is between 6 mm to 12 mm in air; and, it takes a few milliseconds to deliver one spot, a few seconds for one energy layer, and a few minutes for one beam. The beamlets are nearly parallel in the vicinity of the target region 192 and some beam paths are reused to target spots at different depths. Beamlets that share the same path (e.g., same particle scan angle 111) except for differences in depth inside the subject are said to be co-axial. Coaxial beamlets (and beamlets spaced apart by less than the beamlet width) increase the dose delivered to tissue cells of the subject 190 outside the target region 192.

Figure 2:
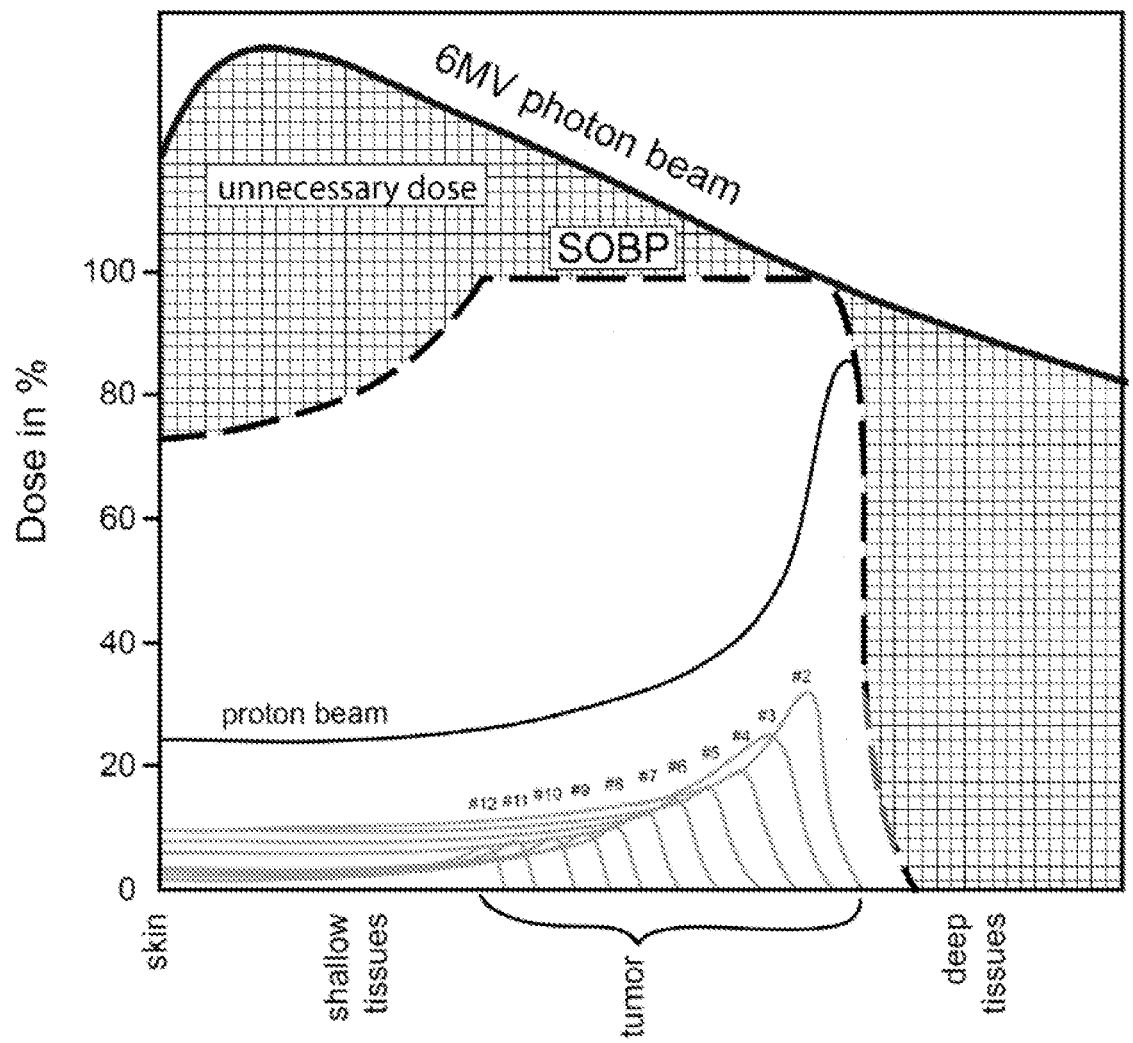
FIG. 2 is a graph that illustrates an example spread out Bragg Peak (SOBP) used in previous approaches.

Because a single Bragg peak covers very little depth of the target region, traditionally particle beamlets are clinically utilized by stacking Bragg peaks from the highest energy (deepest deposition) to lowest energy (shallowest) to create the spread out Bragg peak (SOBP). FIG. 2 is a graph that illustrates an example spread out Bragg Peak used in previous approaches. The horizontal axis indicates depth in subject in arbitrary units from zero on the left and increasing to the right along the beam. Various tissue regimes are labeled from skin to shallow tissue to tumor (target region) to deep tissue. The vertical axis indicates dose delivered in normalized units relative to 100% at the desired dose in the target region. The normalized dose delivered by each individual coaxial proton beamlet is indicated by traces, in which the deepest three are numbered, deepest and largest initial particle energy to shallowest and smallest initial particle energy, as #1, #2, #3. The dashed trace indicates the total normalized dose at each depth by summing the individual doses of the various coaxial proton beamlets. As indicated by the dashed trace, the skin and shallow tissue outside the target region are subjected to significant doses, on the order of 70% to 95% of the dose delivered to the target region, risking damage to cells in these normal tissues, especially when particularly high doses are delivered as in GRID therapy.

Figure 3:
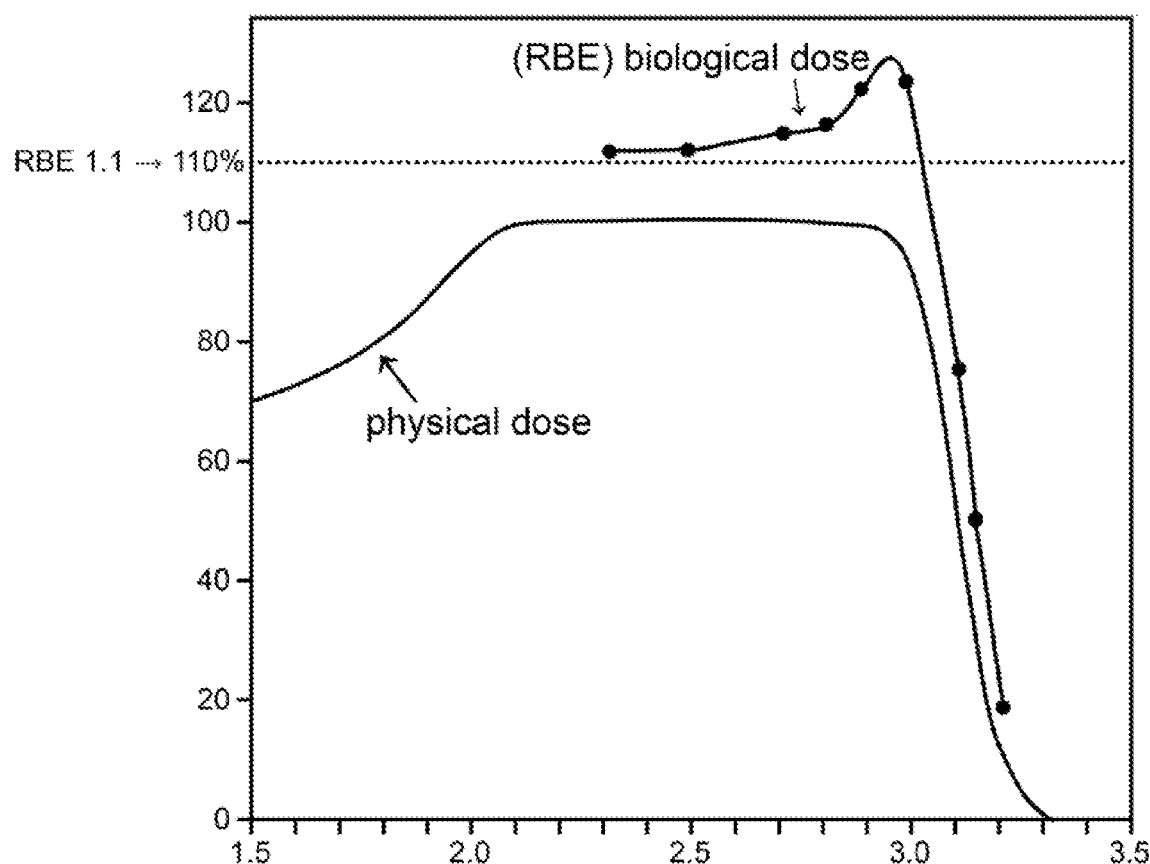
FIG. 3 is a graph that illustrates example radiobiologic effect (RBE), utilized according to an embodiment.

The end of range of a Bragg Peak is believed to have a higher radiobiologic effect (RBE) than the plateau of the SOBP (Buchsbaum App Radiat Oncol 2013). FIG. 3 is a graph that illustrates example radiobiologic effect (RBE), utilized according to an embodiment. The horizontal axis indicates depth in centimeters (cm) if the beamlets were to be directed at water, which is a surrogate for animal tissue, including human tissue; and, extends from 1.5 to 3.5 cm. The vertical axis indicates dose delivered in normalized units relative to 100% at the desired dose in the target region, where 100% indicates 2 grey (Gy), and extends from 0 to about 130%. A grey (Gy) is a derived unit of ionizing radiation dose in the International System of Units (SI). It is defined as the absorption of one joule of radiation energy per kilogram of matter. The line trace indicates a SOBP, such as depicted in FIG. 2. The circles indicate dose required to kill tumor cells in vitro (called the biological dose) for the observed tumor cell kill rates at the plotted depths of the target region. The kill rates are higher than expected given the physical dose. As a result, proton beam dose is normalized to photon radiobiologic effect or cobalt Gy equivalents and described as either Gy(RBE) or Gy(CGE). The correction commonly used is to multiple proton physical dose by a factor of 1.1 to calculate Gy(RBE). This increase in RBE at the end of the SOBP is currently poorly characterized and not well-quantified. It is thus considered here that the current treatment plans that place the end of the SOBP outside the target region is disadvantageous because such plans put this higher kill zone outside the target region, and presumably in normal or critical tissue.

In addition, there are potential advantages in non-homogenous dose delivery in a target region, especially when the target tissue is a tumor. In clinical applications of GRID radiotherapy (using X-ray photons instead of particles with a rest mass), providing heterogeneous doses in the target region with extremely high peak dosages, an important phenomenon has been observed. Despite the highly heterogeneous dose of a GRID distribution, generally, uniform tumoral regression is observed. In attempting to clarify the semantics surrounding such effects, three mechanisms have been identified: abscopal, bystander, and cohort effects.

Abscopal effects have been rarely documented in the radiotherapy literature; however, they describe tumoral response in a lesion born of the same malignancy but distant from the target tumor being irradiated. In recent years, with the increased utilization of immunotherapy, there has been growing interest in revisiting this effect, yet, there remains relatively limited data as to how to induce it. Recent presentations have suggested that abscopal responses may be immunologically based and best elicited with high dose-per-fraction approaches. Serological markers of immune activation in the setting of stereotactic ablative radiotherapy (SABR) seem to confirm this. Also, delivering very low doses to the non-target tumor seems to augment the abscopal effect. GRID therapy is particularly suited to delivering very high doses to parts of a tumor (peaks) and much lower to others (valleys). These effects are expected to be amplified by use in conjunction with approaches or immunotherapy enhancements.

The bystander effect describes the cell signaling induction brought forth by areas of high dose in GRID radiotherapy that affect nearby cells in the low dose region. Such bystander factors involve cytokines like TNF-$\alpha$, TRAIL, and ceramide, and have each been shown to be induced by GRID approaches. These factors are subsequently involved in initiating the cell death cascade. Both in vitro and in vivo models have confirmed the cellular stress, DNA damage, and cell death outside of the irradiated regions but effected by GRID radiotherapy techniques.

Finally, cohort effects describe more direct cell-cell communications, often through gap junctions, that cause cell death within an irradiated volume. This pathway is more relevant amongst subpopulations where the majority of cells are exposed to a killing dose.

Outside of these explanations, GRID data to date has also suggested that this approach can increase overall tumor oxygenation, an effect that can persist for a substantial portion of any planned subsequent conventionally fractionated course. Additionally, within the particularly high-dose peaks (>10 Gy) of GRID radiotherapy, endothelial cell apoptosis and vascular compromise have been observed. Increased overall oxygenation would lead to increased sensitivity to radiotherapy in viable tumor cells, while vascular compromise adds another dimension of cell-killing in peak regions.

In summary, there are numerous mechanisms by which GRID radiotherapy affects the tumor microenvironment and causes tumoral cell death and response.

2. METHOD OVERVIEW

It is herein expected that each of the effects of GRID radiotherapy is either equally triggered or enhanced by the utilization of particle therapy for spatially heterogeneous delivery, called spatially fractionated particle beam therapy herein. According to various embodiments, a treatment plan for a subject is determined or implemented, or both, using Particle GRID techniques that reduce or eliminate coaxial beamlets or place the edge of a Bragg Peak entirely inside the target region, while generating spatially fractioned peaks of high dose inside the target region, as in GRID radiotherapy. A beamlet in a treatment plan that is not coaxial with any other beamlet in the treatment plan is called a pristine beamlet herein.

Figure 4:
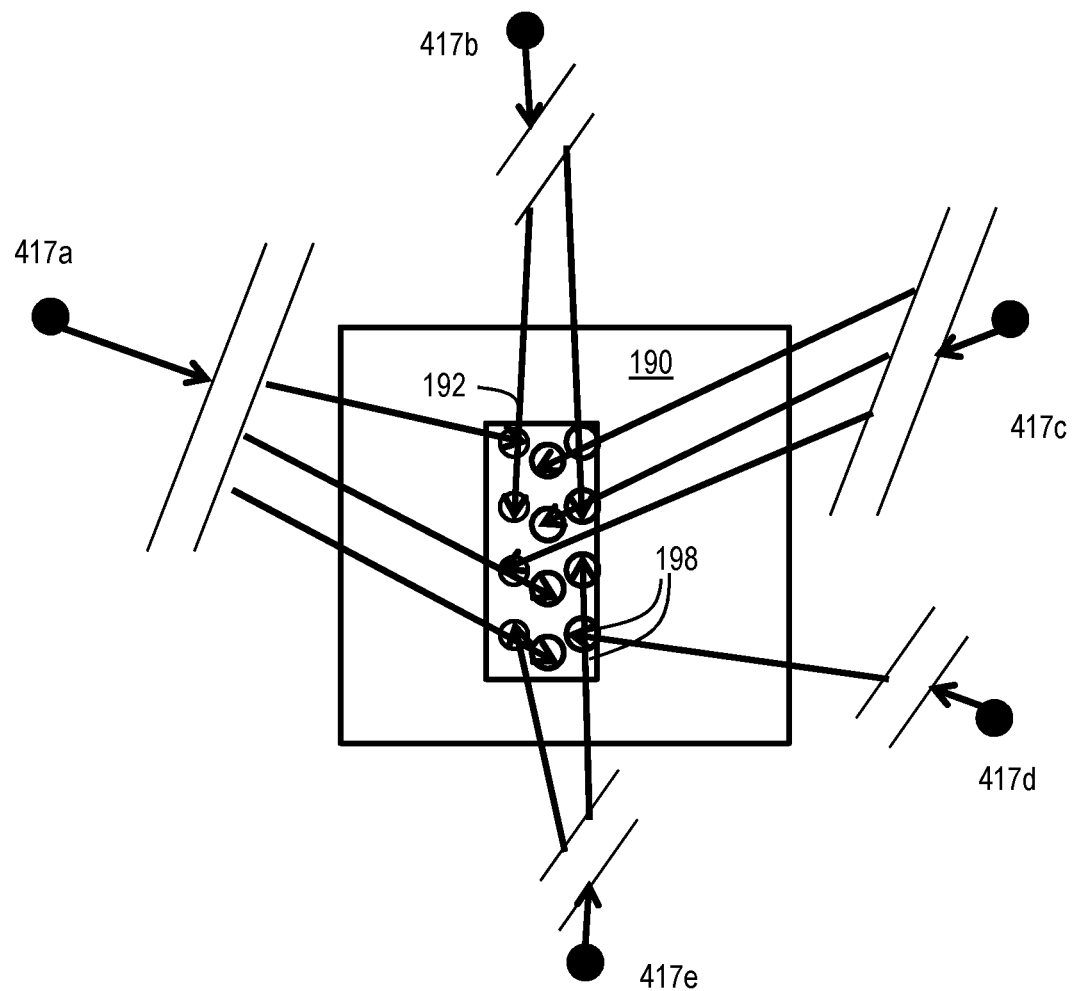
FIG. 4 is a block diagram that illustrates example use of pristine beamlets according to an embodiment.

FIG. 4 is a block diagram that illustrates example use of pristine beamlets, according to an embodiment. Unlike FIG. 1D in which the target region 192 in subject 190 is irradiated from one radiation source origin 117 having a single axis 109, in FIG. 4 multiple different source origins, e.g., 417a, 417b, 417c, 417d, with corresponding different beam axe angles, are used. As a result, the spots 198 in the target region 192 are irradiated with a Bragg Peak at the arrow head of each beamlet, or the intersection of one or more beamlets (cross fire), to produce peaks in dose using beamlets that not only are not coaxial (and therefore are pristine) but also are further apart than in FIG. 1D. In addition, the spots targeted for Bragg peaks, or intersections of two or more beamlets, are distributed more widely apart than in FIG. 1D to take advantage of pass through radiation just before a Bragg Peak and the bystander effect to provide collateral damage inside the target region. The treatment plan illustrated in FIG. 4 is not optimal in any way and there is plenty of opportunity to use coaxial beams if the selection of beamlets is not done carefully. There may also be portions of the target region that are not irradiated sufficiently to meet minimum dosage objectives. So in some embodiments, an iterative process is used to vary the chosen beamlets to minimize the difference from treatment objectives. In some embodiments, the spots selected for a Bragg Peak or intersection of crossing beamlets are arranged to prevent the use of coaxial beamlets for any particular choice of multiple different sources with corresponding different beam axis angles, and thus allow the use of existing software to target an arbitrary arrangement of spots.

Figure 5:
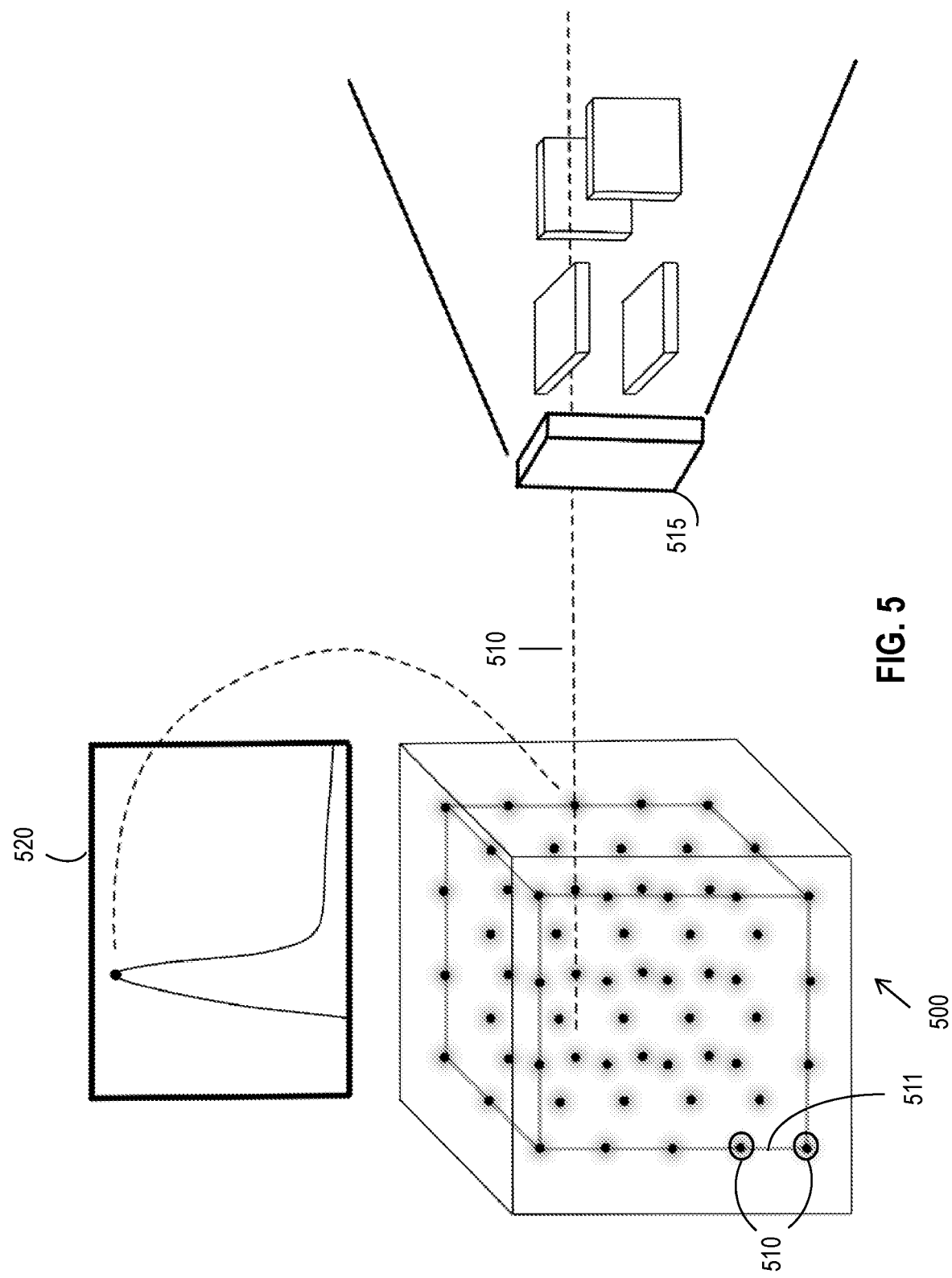
FIG. 5 is a block diagram that illustrates a example distribution of candidate spots inside a target volume (a 3D target region), according to an embodiment.

FIG. 5 is a block diagram that illustrates an example distribution of candidate spots 510 inside a target volume (a 3D target region) 500, according to an embodiment. Each candidate spot represents the target volume receiving a high dose from a Bragg Peak, of extent given by a width of a peak plotted in diagram 520, and is centered on a point in a regular grid. The spacing 511 between adjacent points is larger than the width of the Bragg Peak in diagram 520 to allow for spatially fractionated peaks and valleys in the target region 500. The spots receive exceptionally high doses while the spaces between the spots receive lower doses due to the portion of the beamlet just before the Bragg Peak for the beamlet. A representative beamlet 510 is emitted from the scanning pencil beam source 515 with an initial energy to achieve a Bragg Peak at the spot at the terminus of the beamlet 510. A 2D image of a view directed along a central beam axis from a beam source is called a beam's eye view (BEV). The spots in a beam's eye view can be irradiated by a scanning beamlet with the source in that position. Note that, without rotating this grid of candidate spots, SOBPs would be generated—substantially raising proximal tissue dose and normal tissue damage.

According to some embodiments, a regular grid in the vicinity of an isocenter is rotated with respect to one or more axes through the isocenter, such as around the coordinate x or y or z axes, or some combination. In some embodiments, the grid is rotated about one or more beam axis angle through the isocenter in addition to or instead of one or more of the coordinate axes. The rotation is performed to move the spots on the grid to avoid spots that line on the same beamlet axis from any of an arbitrary set of two or more beam axis angles, i.e., avoid spots that have the same 2D coordinates on a BEV from that beam axis angle. Thus, no two spots lie on the same coaxial beamlet and a treatment plan to irradiate each spot using those beam axis angles will avoid coaxial beamlets and thus achieve coverage with only pristine beamlets. It is often advantageous to select the arbitrary beam axis angles to be about 90 degrees or more apart, as in FIG. 4.

Figure 6A:
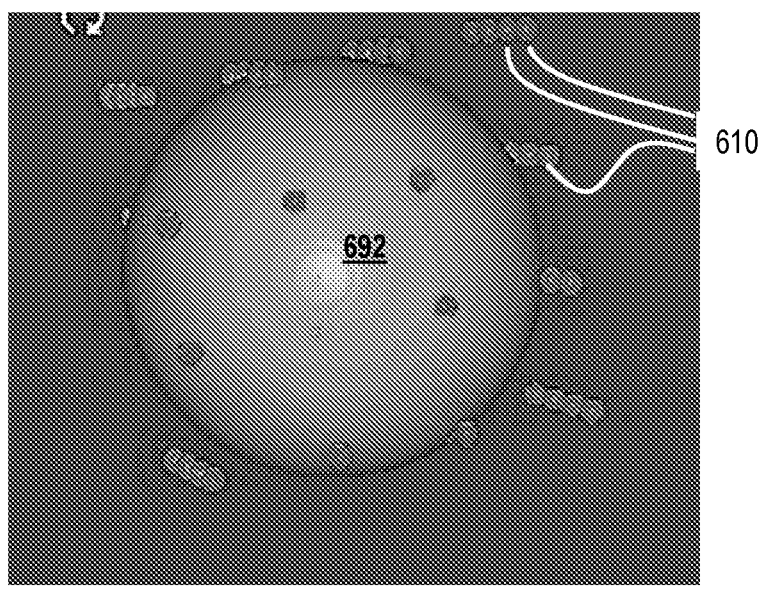
FIG. 6A is a block diagram that illustrates an example distribution of spots and a target so as to span a target region, according to an embodiment.

FIG. 6A is a block diagram that illustrates an example distribution of grid candidate spots 610 and a spherical target region 692 so as to span a target region, according to an embodiment. The target is opaque in this presentation to give the reader a sense of the three dimensions involved, so spots inside the target are not evident, but it is clear the regular grid continues through the target.

Figure 6B:
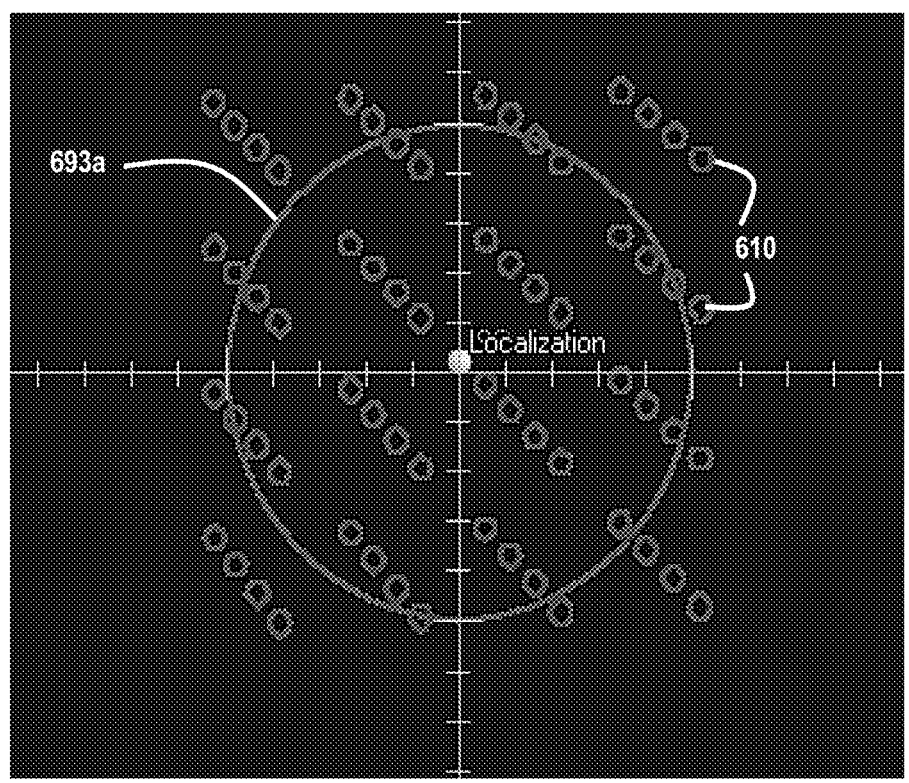
FIG. 6B is a block diagram that illustrates an example distribution of rotated spots in one beam's eye view, according to an embodiment.
Figure 6C:
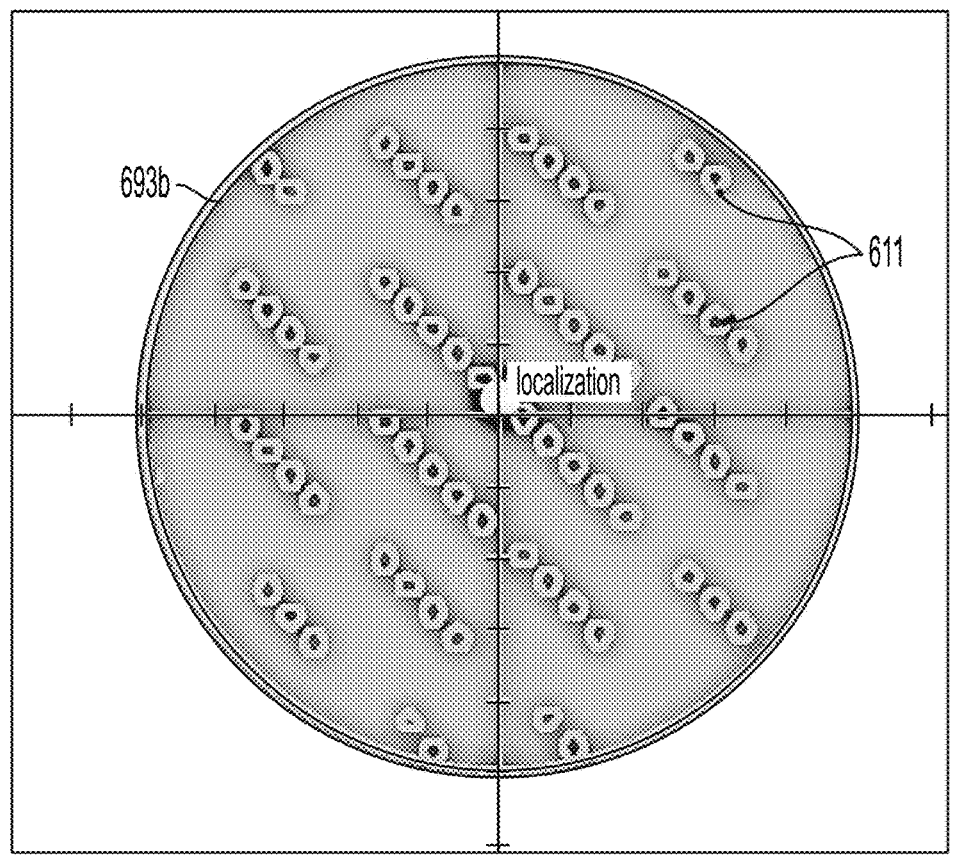
FIG. 6C is a block diagram that illustrates an example distribution of rotated spots in a different beam's eye view after removal of spots outside a target region, according to an embodiment.

FIG. 6B is a block diagram that illustrates an example distribution of rotated spots in one beam's eye view, according to an embodiment. This 2D beam's eye view is for one of just a few different beam axis angles. In this beam's eye view, the maximum extent of the target region is indicated by a circle 693a and the candidate spots 610 are more clearly separated than in FIG. 6A so there is no overlap, thus better separating the beamlets scanned from the corresponding position of the source origin and reducing collateral damage. Candidate spots 610 outside the target region are retained temporarily for this representation. FIG. 6C is a block diagram that illustrates an example distribution of rotated spots 611 in another beam's eye view after removal of candidate spots outside a target region, according to an embodiment. The target region in this view is represented by circle 693b.

Figure 7A:
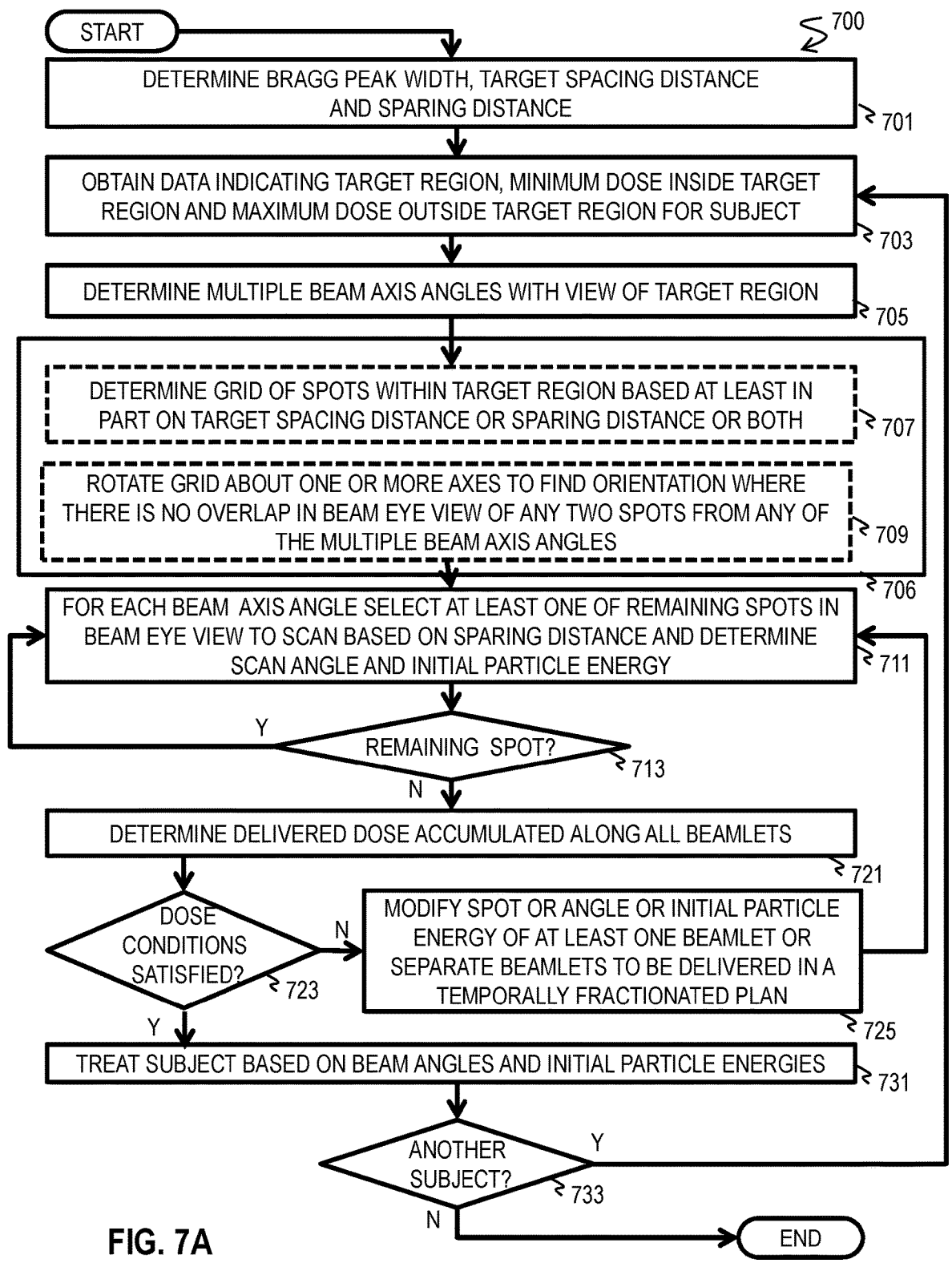
FIG. 7A is a flow diagram that illustrates an example method to determine scan beams for spatially fractionated particle therapy, according to an embodiment.

FIG. 7A is a flow diagram that illustrates an example method 700 to determine scan beams for spatially fractionated particle therapy, according to an embodiment. Although steps are depicted in FIG. 7A, and in subsequent flowchart FIG. 7B, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 701 one or more distance scaling factors are defined. For example, a Bragg Peak width is determined, such as Bragg Peak width at half maximum for the particle beam type in target region tissue type, or Bragg Peak width above a fixed dose, such as 10 Gy. In some embodiments, scaling factors called a target spacing distance and a sparing distance are also defined. Target spacing distance refers to a distance from a peak dose over 10 Gy for which cell death has been observed for a particular tissue type, such as tumor tissue, in a target region of a subject. A typical range of target spacing distances is between about 1 and about 3 centimeters (cm). Sparing distance refers to a minimum distance between peak doses of about 10 Gy or more for which improved tissue sparing in the valley dose region has been observed for a normal tissue type. A typical range of sparing distances is between about 1 and 3 cm. In some embodiments, nominal values of 4 mm for Bragg Peak width, 3 cm for target spacing distance and 3 cm for sparing distance are used. These distances are used in subsequent steps to inform the spacing of spots (e.g., representing target volumes) inside the target region.

In step 703 treatment objective data is obtained. Treatment objective data includes at least data indicating: a target region inside a subject; a minimum dose to deliver inside the target region; and, a maximum safe dose not to be exceeded inside the subject but outside the target region. In some embodiments, other regions of different maximum safe dose outside the target area but inside the patient are also provided, e.g., for critical organs the maximum safe dose may be lower than in less critical organs. Any method may be used to obtain this treatment objective data, including receiving manual input from a user in response to a prompt or unsolicited, or retrieval from storage on a computer-readable medium, either locally or remotely, or in a message from another process, on a local or remote computer system or chip set, either unsolicited or in response to a request message.

In step 705 multiple beam axis angles with a view of the target region are determined. Each beam angle has an associated isocenter, gantry angle, couch angle, couch elevation and couch horizontal displacement. Gantry angles are most easily and rapidly changed during a treatment. Typically, several beam angles have corresponding different gantry angles but the same couch angle, couch elevation and couch horizontal displacement. Often, the different beam axis angles correspond to different gantry angles about 90 degree or more apart, such as three angles 120 degrees apart, or four gantry angles 90 degrees apart. Any method may be used to obtain a number and beam axis angles, including receiving manual input from a user in response to a prompt or unsolicited, or retrieval from storage on a computer-readable medium, either locally or remotely, or in a message from another process, on a local or remote computer system or chip set, either unsolicited or in response to a request message.

In step 706, a set of spots of finite (non-zero) width are determined to span the target region. In other embodiments, fewer or more spots are engaged for the method 700. For example, in some embodiments, only some spots are irradiated with pristine beamlets, but other spots or a background is irradiated using different methods, such as with a SOBP or radiotherapy, or at different times. Each spot is to receive a Bragg Peak from a pristine beamlet or an intersection of two or more pristine beamlets (cross fire). In some embodiments, the width of the spots is related to the width of the Bragg Peak, determined in step 701. For example, each spot is a sphere with a diameter equal to the Bragg Peak width. The Bragg Peak width may be modified by the treatment system/technology, collimators, etc. In some embodiments, the spots are 3 mm diameter spherical contours. Once the physician has delineated the gross tumor or target region, this region is contracted, isotropically or non-isotropically, to create a safety margin at the edge of the tumor in which no peaks will be targeted. Dose fall-off may be allowed to cover this "no-fly zone". The distance of contraction is dependent upon the size of the tumor, reproducibility of setup, and depth (range uncertainty) of the tumor. Thus, due in part to bystander effects, in some embodiments, the spots determined span a region smaller than the target region by a contraction distance related to the target spacing distance. This volume becomes the planning target volume (PTV) for the Particle GRID plan.

In some embodiments, the spots are so positioned that some are coaxial on some scan beam directions on one or more different beam axis angles determined in step 705, but the beamlets actually added to the treatment plan are filtered to avoid using coaxial beamlets, as described in more detail below with reference to step 711. Thus only pristine beamlets are included in a treatment plan using the Particle GRID techniques. Particle GRID techniques can be combined with other radiotherapy or particle beam therapy (such as SOBP) or immunotherapy or some combination in some embodiments.

In some embodiments, spots re positioned such that no two spots are coaxial on any beamlet from any of the selected beam axis angles. Said another way, this means that no two spots are coaxial in a beam's eye view along any of the plurality of beam axis angles. Preferably, the finite width spots do not overlap at all in any of the beam's eye views of the selected beam axis angles to better separate the beamlets outside the target region.

In an example embodiment, a grid of spots that span the PTV are rotated relative to one or more axes, e.g., the x axis or y axis or z axis of coordinate system 130, or some combination, until no spots are coaxial in any beam's eye view of the multiple beam axis angles. In these embodiments, step 706 includes steps 707 and 709. In step 707, a grid of candidate spots that span the target region are determined with regular spacing. In some embodiments, the regular spacing is based on the Bragg peak width or the target spacing distance or the sparing distance, or some combination. For example the spot size has a diameter of the Bragg Peak and the spacing between adjacent spots on the grid is the target spacing distance to encourage kills in all intervening cells. In some embodiments, even wider spacing can be tolerated, for the reasons given above on experience garnered from GRID radiotherapy, and then the spacing between the center of the spots on the grid can be expanded to that of the sparing distance or greater so that when projected on the beam's eye view for most if not all of the beam axis angles, the spots are separated by at least the sparing distance, allowing all spots to be targeted on every beam axis angle. In step 709 the regular grid is rotated about one or more axes to find an orientation of the grid such that there is no overlap of any two spots in a beam eye view of the grid at any of the multiple beam axis angles.

Figure 7B:
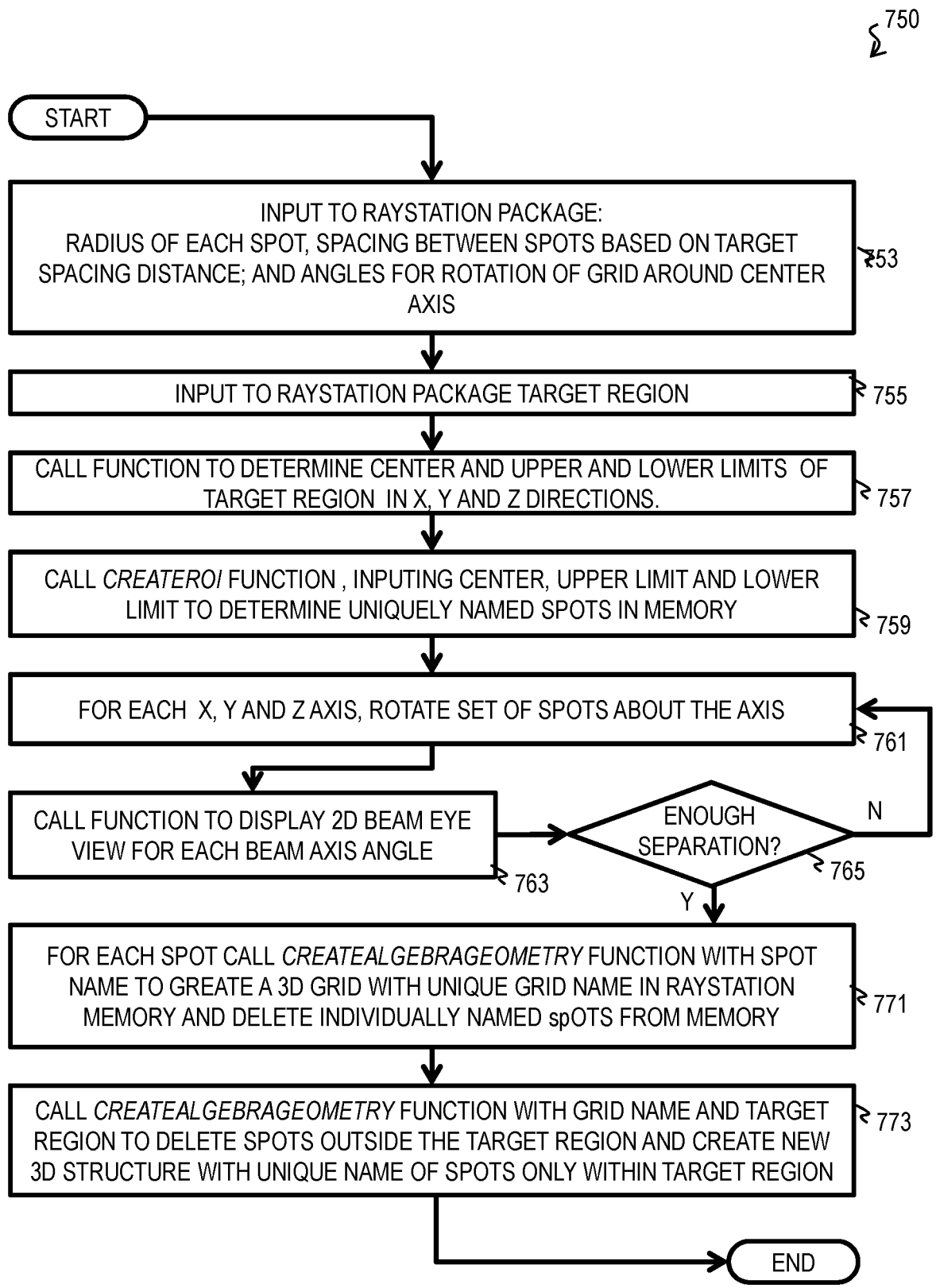
FIG. 7B is a flow diagram that illustrates an example script for generating a distribution of rotated spots, according to an embodiment.

An advantage of a regular grid rotated to avoid coaxial scan beam angles is that some existing automated tools for radiation therapy planning can be used to select the spots during step 706. A script using such tools is described below with reference to FIG. 7B. FIG. 7B is a flow diagram that illustrates an example script 750 for generating a distribution of rotated spots, according to an embodiment. In this embodiment the RAYSTATION® treatment planning package is used, available from RAYSEARCH® Laboratories of Stockholm, Sweden.

In step 753 a user inputs manually the radius of each spot, the spacing between spot surfaces (e.g., based on target spacing distance or sparing distance or some other factor, or some combination) and angles for rotation of the grid around the x axis or y axis or z axis at the isocenter. In step 755, the target region is read, e.g., from the treatment objective data 152. In step 757, a function is called to determine the minimum, center and maximum values of the target region in the x, y and z dimensions.

In step 759, the CreateROI function is called with the minimum, center and maximum in each of the x, y and z dimension to generate a set of evenly space spots with unique identifiers (names) in which the set encloses the target region. For example, as depicted in FIG. 5, a grid of spots 510 of finite width is generated.

In step 761 another function is called that rotates the set of points about the x axis, y axis and z axis through the isocenter, respectively, by one of the angles specified in step 753, such as depicted in FIG. 6B, with a spherical target region imposed. In step 763 a 2D display function is called with a particular beam axis angle, e.g., entered manually, to display a 2D beam's eye view for that beam axis angle, such as depicted in FIG. 6B. This is repeated for the all the beam axis angles in the plan. In some embodiments, several candidate beam axis angles are considered during step 763 before a decision is made on which few beam axis angles to use in the treatment plan. In step 765, the user inspects the beam's eye view to ensure that there is sufficient separation of the spots in at least two of the beam's eyes views. If not, control passes back to step 761 to rotate the set of points differently, e.g., using an increment of the angles for rotation provided in step 753 for at least one of the x or y or z axis through the isocenter.

When, for example, two beam axis angles are found for which each beam's eye view shows sufficient separation, then control passes to step 771. In step 771 the current rotations of the set of points is locked in, and, for each finally positioned and uniquely named spot, the function CreateAlgebraGeometry is called to form a 3D grid structure in suitable coordinates. That 3D structure is stored in memory under its own unique identifier (name) The individual uniquely named spots are removed from memory.

In step 773, the function CreateAlgebraGeometry is called again to form a new 3D grid structure with candidate spots outside the target region eliminated; and, that new 3D structure is stored in memory under its own unique identifier (name) The old uniquely named 3D structure is removed from memory. A beam's eye view of the new 3D structure with an outline of the target region in that view is depicted in FIG. 6C.

Thus, using the example script of FIG. 7B, a set of spots are determined in steps 707 and 709 that are not coaxial in any beam's eye view of the corresponding beam axis angle (e.g., gantry angles).

Returning to FIG. 7A, after the spots are selected in step 706, in step 711 the beam eye view of each beam axis angle is reviewed in turn. For each beam eye's view, a pristine beamlet is added to the treatment plan with corresponding scan beam angle and particle initial energy to direct a Bragg Peak at a spot. The initial energy depends on the distance from the surface of the subject to the position of the spot along the angle of the beamlet. The beamlet is pristine if it does not share a scan beam angle with any other beamlet of the current beam axis angle. In some embodiments, all spots are defined to avoid any coaxial beamlets, so every spot can be addressed by beamlets on each beam axis angle and those beamlets will automatically be pristine. In some embodiments, to prevent damage to tissue outside the target region but inside the subject, the added pristine beamlet is required to be at least a minimum distance from any other beamlet; e.g., in the beam's eye view the spots must be separated by at least this minimum distance. In some embodiments, the minimum distance is based on the sparing distance, such as being equal to the sparing distance.

In some embodiments, all spots are defined to not only avoid any coaxial beamlets but also ensure at least a sparing distance between spots in each of one or more selected beam axis angles. In such embodiments, every spot can be targeted at such a beam axis angle and still ensure safe separation of beamlets inside the subject and outside the target region. In some such embodiments, a single beam axis angle for which all spots are separated by at least the sparing distance treatment makes up the treatment plan. In other such embodiments, one or more additional beam axis angles are added to the treatment plan to better fill in the target region with at least a minimum dose.

In step 713 it is determined whether any spots remain without either a Bragg Peak or at least an intersection of two or more pristine beamlets. If so, control passes back to step 711 to march through the multiple beam axis angles again and target any such remaining spots.

The treatment plan derived above is more likely to have several desirable features, including: 1) using only pristine beamlets to spare the subject outside the target region; and 2) spatially fractionated dose delivery to take advantage of the higher kill rates associated with very large peak doses. However, it is not guaranteed that the dose delivered will satisfy any or all the treatment objectives received in step 703, nor is the difference from the treatment objective, if any, quantified. Thus in some embodiments, the method 700 includes a dose determination or adjustment or optimization loop comprising one or more of steps 721, 723 and 725. In other embodiments, all these steps are omitted; and, control passes from step 713, "NO" branch, to step 731, described below.

In step 721, dose delivered to each picture element (pixel) inside the patient is determined by summing the computed doses along all beamlets resulting from the last execution of step 711. In general, pixel size is smaller than spot size in order to generate an image of dose distribution that resolves the Bragg Peaks. Any method to measure or simulate this accumulated dose may be utilized. For example, a Zebra® device by Ion Beam Applications (IBA, Ottignies-Louvain-la-Neuve, Belgium) may be utilized to verify dose delivery.

In step 723, it is determined how far the spatial distribution of accumulated dose falls short of the treatment objectives. If the discrepancy is large enough, then control passes to step 725. In step 724 one or more of several adjustments are made, either manually or automatically (e.g., using one or more known optimization approaches), or some combination.

In some embodiments, one or more spots are changed, either eliminated to reduce damage outside the target region, or added to treat under-dosed portions of the target region, or moved from an excessive peak portion to under dosed portion of the target region. For example, the spacing of spots within the target may be adjusted to raise or lower the valley doses between peaks as well as to modify the mean dose across the target as a whole. After such spot array adjustments, control passes back to step 711 to again select pristine beamlets to address the new set of spots.

In some embodiments, one or more beamlets are changed in terms of target spot or intensity or initial particle energy or beam diameter. Modulating the diameter of the beamlet is advantageous because there is emerging evidence regarding the utility of particle beams of various sizes (called mini-beams or microbeams or macrobeams for large spots) and their comparative RBEs. Control then passes back to step 711 to again select pristine beamlets to address any remaining uncovered spots.

In some embodiments, spots that contribute to too many beamlets too close together in the tissue inside the subject but outside the target region are removed from the treatment plan and placed into a treatment objective for a later treatment, essentially introducing a new temporally fractionated element to the treatment plan. In some embodiments some combination of spot location changes, beamlet property changes or temporal fractionized plans is used during step 725.

If it is determined in step 723 that the discrepancy between the delivered dose and the treatment objectives is tolerable, then control passes to step 731. In step 731, the treatment plan comprising the final set of beam axis angles and beamlets, is stored for use by a particle therapy apparatus. It is often efficient for the gantry angle and couch to be moved to the first beam axis angle, and while at that first beam axis angle, first scan all beamlets of a largest initial energy value in the 2D beam's eye view, followed by all beamlets of the next largest initial energy, and so on until the beamlets directed to the nearest spot are scanned. The beam axis angle is then changed to the next closest beam axis angle, e.g., by rotation the gantry or moving the couch, or some combination under the control of the treatment plan produced by the above methods. For example, in some embodiments the subject is placed on the couch and the particle therapy apparatus operated in order of increasing gantry angles and from highest to lowest initial particle energies according to the set of beamlets last derived in step 711 that satisfies the dose conditions to treat the subject.

In step 733, it is determined if anther subject or different target region in the same subject is to be treated using the Particle GRID techniques. If so, control passes back to step 703 to receive treatment objective data. Otherwise, the process ends.

Thus, these Particle GRID techniques prevent stacking of beamlet entry points, and more of a substantial portion of the RBE is positioned within the target. This may involve moving the patient relative to the particle beam, whether translationally or rotationally. Lateral dose falloff (penumbra) would fill in the valleys of the heterogeneous distribution. Use of multiple beams would allow for interleaving/intertwining of these beamlets to produce tight/conformal distributions with the desired peak to valley ratios. There are numerous plans/distributions that may achieve this central principle, and numerous beam or arc techniques are feasible, yet, to date, this is mostly designed with a limited number of beams/angles (2-3 beams). With Particle GRID techniques, peaks may either be created by the end of range of a Bragg peak in the current design or by overlapping entrance dose from different entrance angles (cross-fire).

The Particle GRID technique offers a number of expected advantages over traditionally delivered particle therapy, particle therapy-based LATTICE techniques, and photon-based GRID therapy. In comparison to traditional particle therapy, this technique avoids the spread out Bragg Peak (SOBP) approach and therefore lowers entrance doses overall, protecting more normal tissue despite high doses delivered within the tumor. This technique also provides regions of proximal tissue between beamlets that are spared from high doses and therefore will likely heal better and heal into the regions within the beamlets. The end of range for the pristine Bragg peaks falls within the gross tumor whereas with traditional SOBP arrangements, this, by design, falls within the safety margin which is normally positioned beyond and around the tumor and within an organ at risk or critical structure.

When compared with particle therapy based LATTICE/GRID techniques that have been described, the current approach would offer better geometric spacing of the peaks with more modulation possible, improved proximal dose falloff and therefore better organ at risk/skin/soft tissue sparing, and more pronounced end of range, high RBE depositions within the target with likely more dramatic RBE increases. Compared to the more commonly employed photon techniques, Particle GRID is expected to offer substantial mean dose increases within the tumor over 3-dimensional conformal radiotherapy techniques. Even over intensity modulated radiation therapy (IMRT), the peaks with Particle GRID are expected to be higher, the valleys more controlled, the RBE higher, and the critical structure dose dramatically lower. The relative lack of exit dose is especially advantageous in achieving the desired dose distribution.

Overall, Particle GRID offers substantial advantages over any currently described or employed technique for the delivery of spatially fractionated radiotherapy. It has the potential to substantially improve tumoral cell kill, and therefore, outcomes in especially bulky, hypoxic, or radio-insensitive tumors. Particle GRID is able to optimize delivery of spatially fractionated radiotherapy with particle beams to improve tumoral cell kill, RBE, tumor control, and patient outcomes especially in the setting of bulky, hypoxic, or radio-insensitive tumors.

3. EXAMPLE EMBODIMENTS

Example embodiments include demonstrating the techniques for proton beam therapy.

Figure 8A:
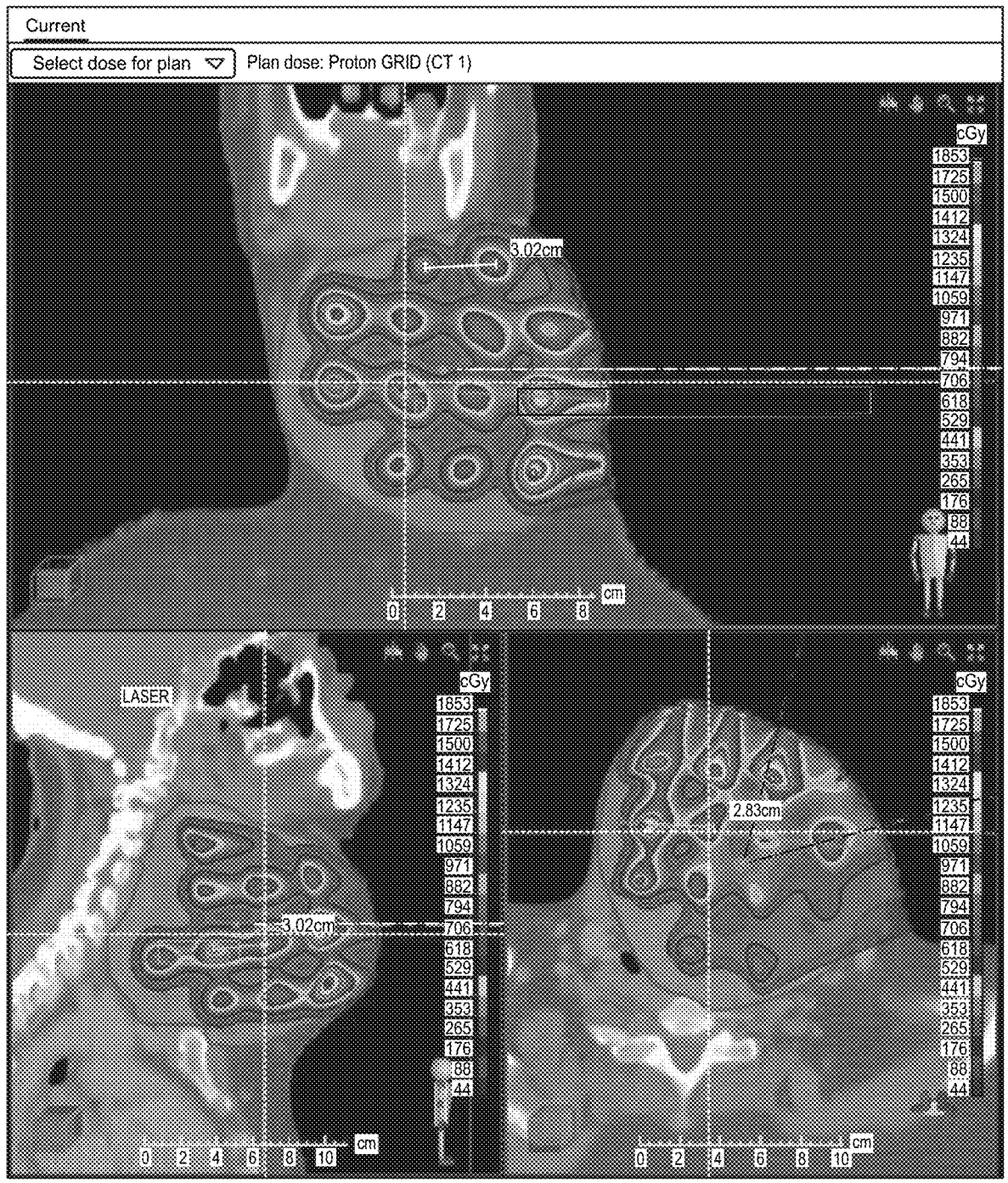
FIG. 8A through FIG. 8C are images that illustrate example spatial distributions of deposited dose and spacing in line profiles therefore, according to example embodiments.
Figure 8A:
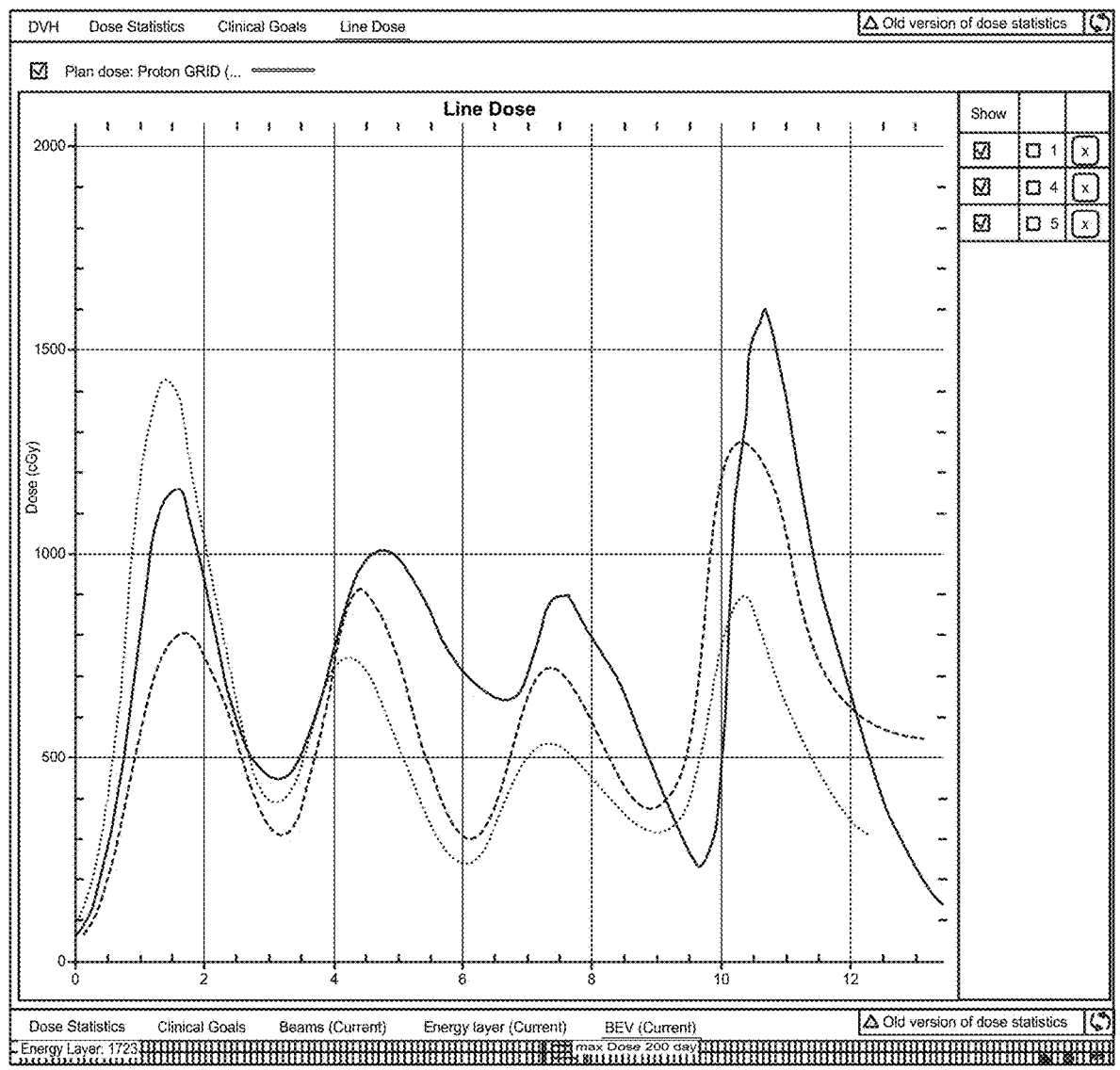
Figure 8B:
Figure 8B:
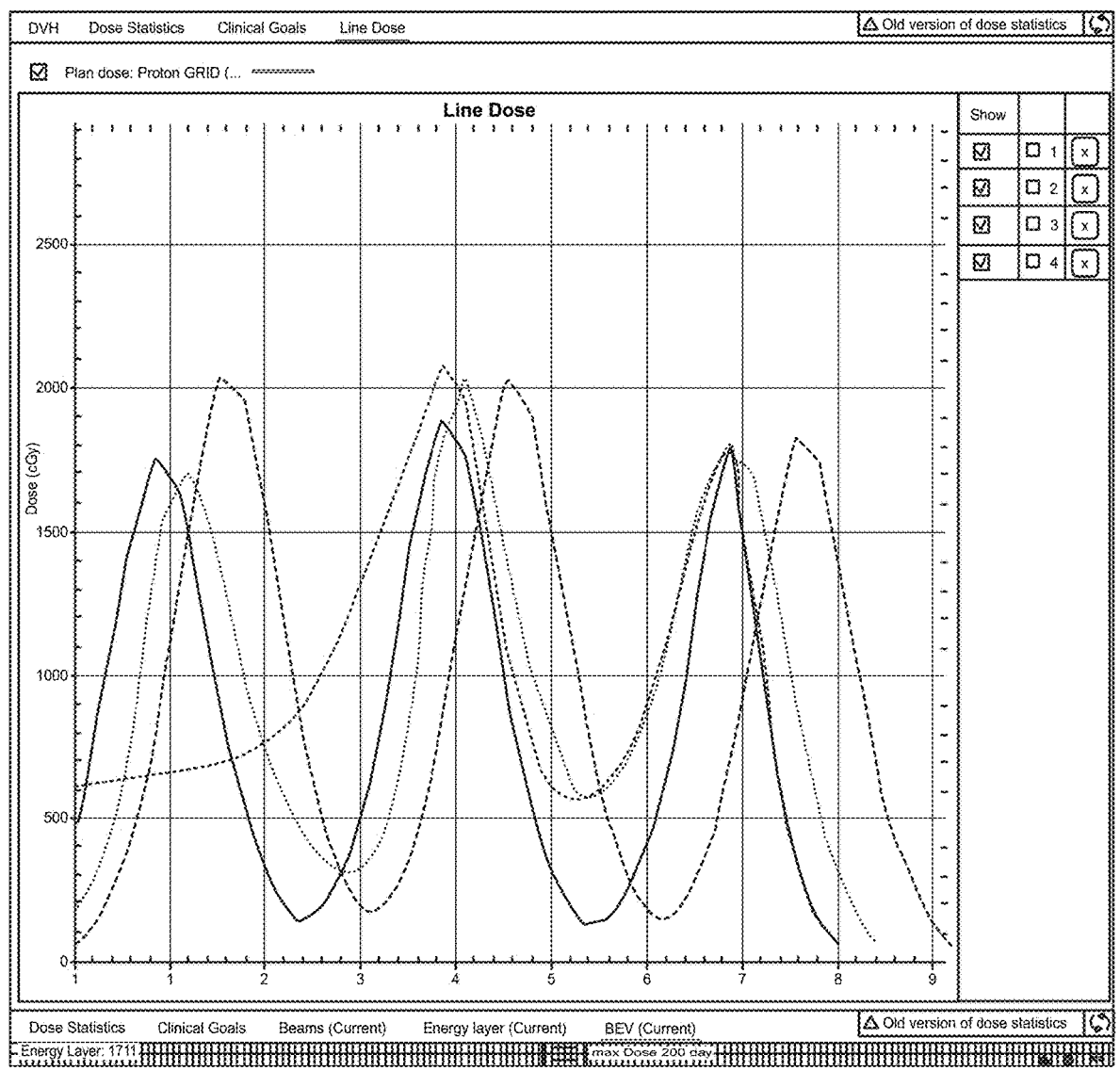
Figure 8C:
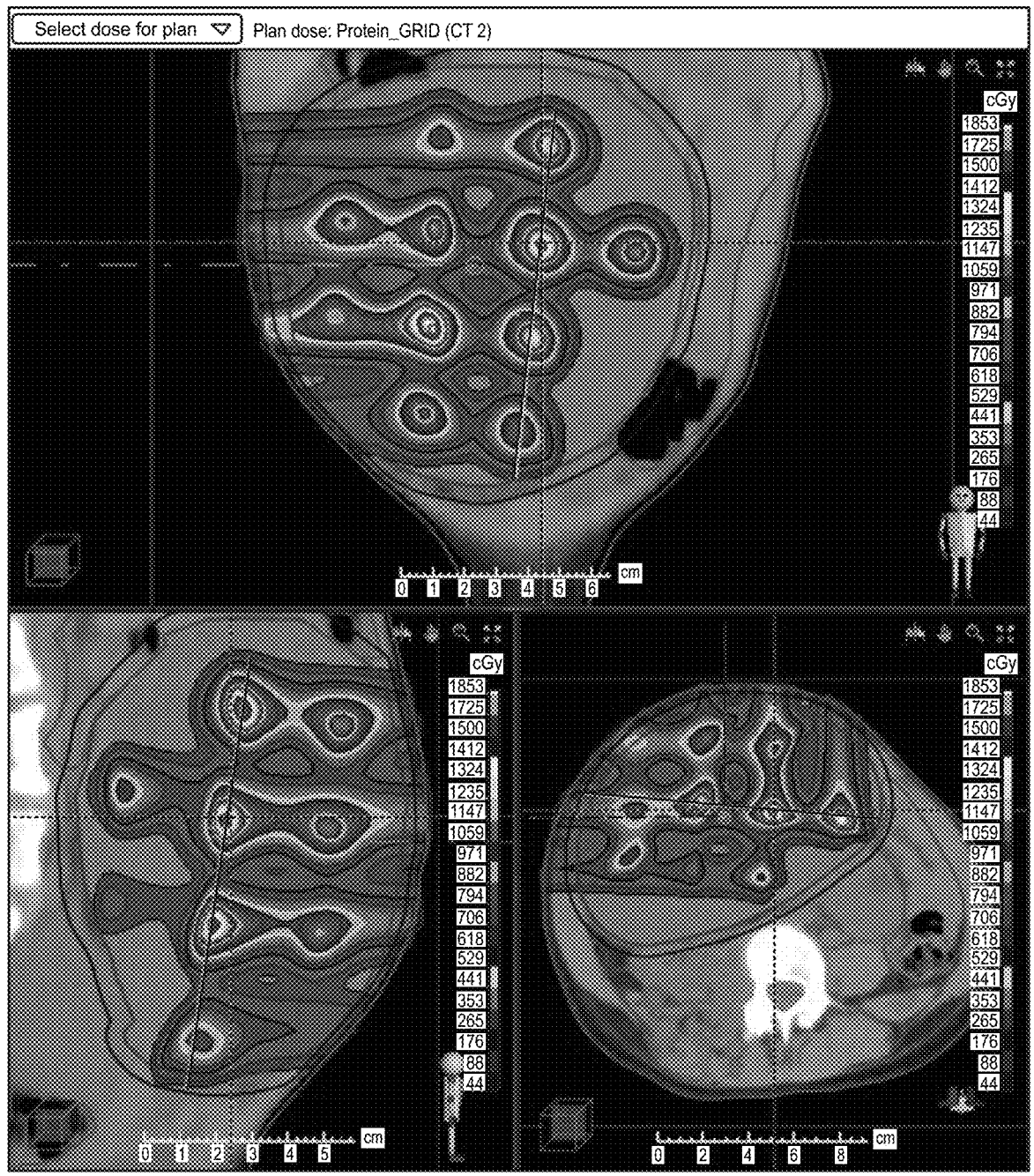
Figure 8C:
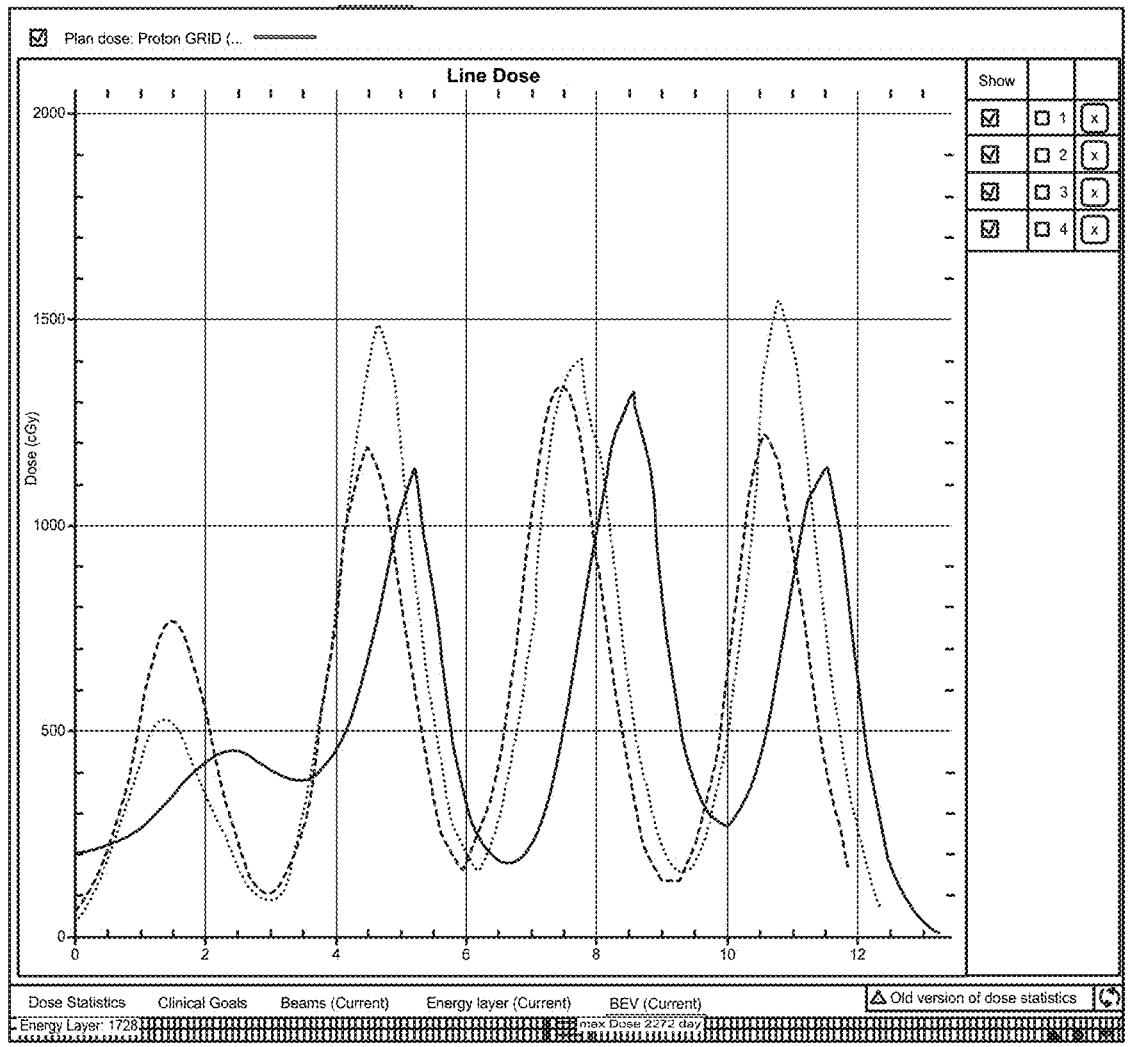

FIG. 8A through FIG. 8C are combined images with spacing charts that illustrate example spatial distributions of deposited dose and spacing in line profiles therefore, according to example embodiments. In each figure, there are three images to the left. The top image is the view from the front of a patient (coronal plane), the left image is the view from the side of the patient (sagittal plane) and the right image is the view toe toward head of the patient (axial or transverse plane). The highest peaks are surrounded by bright rings. To the right of each figure is a plot of dose on a vertical axis versus distance on a horizontal axis for three or more directions through the target area. High peaks are separated by valleys in the target region and doses trend to zero outside. FIG. 8A depicts treatment dose profile and distribution for Particle GRID GRID therapy for a large thyroid tumor. FIG. 8B depicts treatment dose profile and distribution for Particle GRID GRID therapy for a large lung mass. FIG. 8C depicts treatment dose profile and distribution for Particle GRID GRID therapy for a large abdominal tumor.

As shown in these examples, the Particle GRID GRID target spot spacing may be modulated by the user to achieve the desired peak-to-valley ratio within a complete Particle GRID GRID plan. Testing thus far has generally attempted to achieve a 15 Gy peak plan dose with 2 Gy valley doses to simulate, with an integrated 2 Gy uniform dose background in the target region, the approximately 4:1 peak-to-valley profile generally employed with collimator based photon GRID techniques. This has been achieved with approximately 3 cm peak target spacing in each of the x, y, and z directions prior to rotation of the targets to off axis in each of these directions. Example line dose estimations are displayed in FIG. 8A through FIG. 8C. Note that peak targets and doses are intentionally off-axis to each of the axial, sagittal, and coronal planes visible in the treatment planning software, and therefore the line dose graphs do not intersect the center of each of the peaks. Regardless, these figures are illustrative of the target peak spacing principle. The peak height, valley depth, and rate of the transition between the two over distance will be changed based on spacing, target depth, beam angle, peak target size, and water-equivalent thickness of beam path, amongst other factors.

Figure 9A:
FIG. 9A and FIG. 9B are images that illustrate example spatial distributions of deposited dose, according to another example embodiment.
Figure 9B:
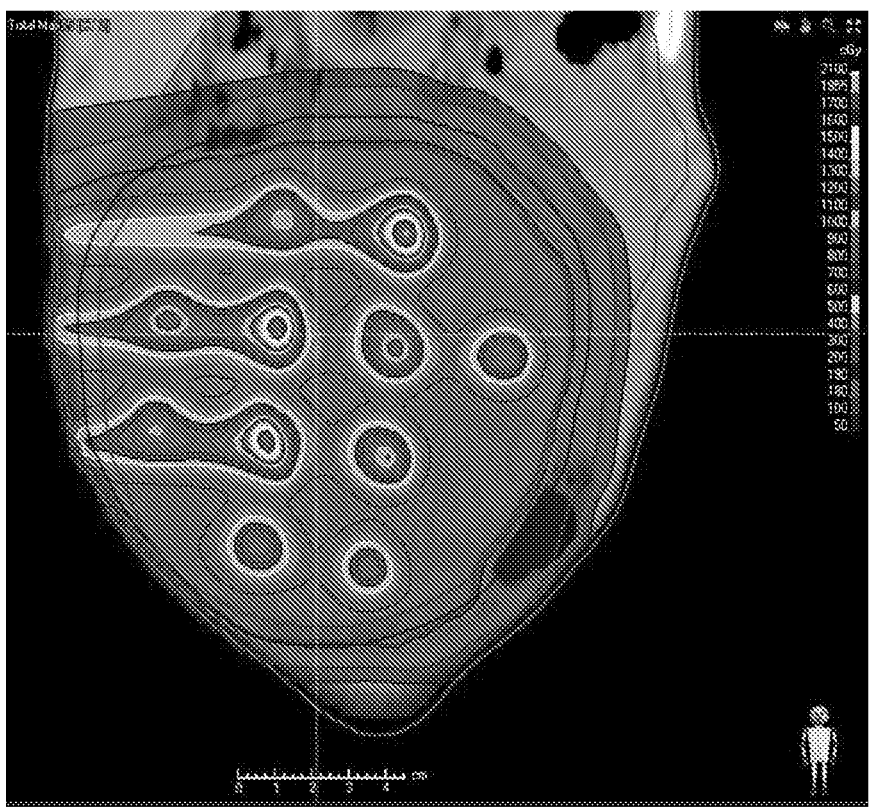

FIG. 9A and FIG. 9B are images that illustrate example spatial distributions of deposited dose, according to another example embodiment. In these images, bright rings encircle the highest peaks. Eleven peaks are evident. In this example, one beam axis angle is from the left in the plane of the image, and the other beam axis angle is perpendicular to the plane of the image. A two beam axis plan by this method generates the distribution depicted in FIG. 9A (partial plan) alone for GRID therapy. FIG. 9B shows more complete coverage inside the target region by a separate plan utilizing the same two beams to deliver a uniform dose across the target, making the Particle GRID a simultaneous integrated boost (SIB) of a normally fractionated plan. If with two beam axes there is still shadowing of targets based on the selected spacing, additional beams can be added to "fill in." In some embodiments, more conventional but limited stacking of coaxial beamlets can be added to the beamlets defined by the Particle GRID techniques. All the peaks are not visible with the available imaging software used to produce FIG. 9A and FIG. 9B because axial, coronal, and sagittal imaging has no plane in which all of the peaks are visible. In this example patient, the lattice of targets is non-coplanar in all of these directions. Thus far, peak-to-valley gradients have been modulated to produce the 4:1 ratio generally recommended for, and achieved with, 2D photon based techniques with collimators. Mean dose across the target can be controlled primarily based on peak spacing and peak maximum doses.

Figure 10:
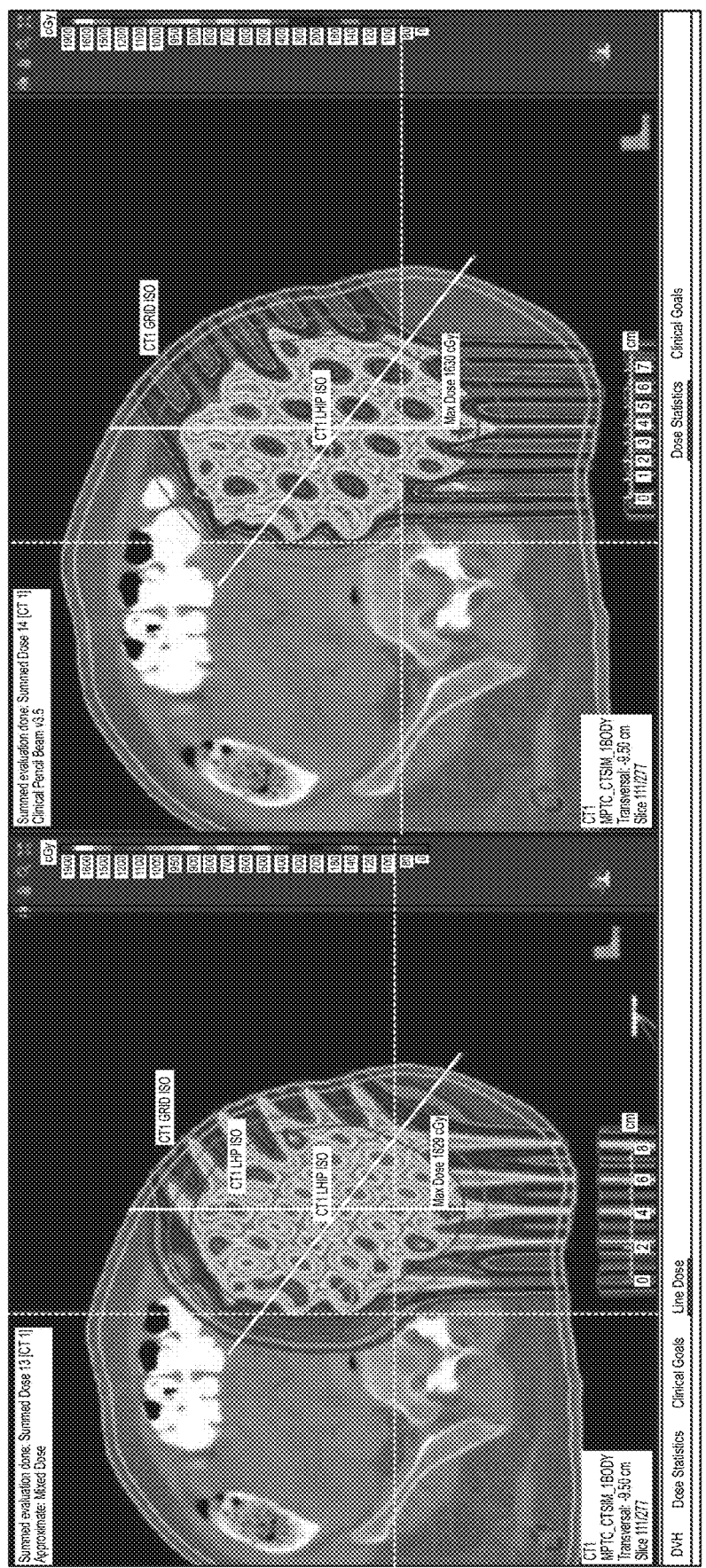
FIG. 10 is an image that illustrates example spatial distributions of deposited dose, according to another example embodiment.

FIG. 10 is an image that illustrates example spatial distributions of deposited dose, according to another example embodiment. In this embodiment, some peaks are created as a result of intersecting (cross fire) beamlets. With six beamlet entering from one beam axis angle (upper left relative to the page) and five from a second beam axis angle (right relative to the page) a large number of peaks and valleys are generated. The upper image shows cross fire peaks in a plane where the beamlet have relatively low initial energy for shallow spots. The lower image shows cross fire peaks with a greater density of beamlet overlap intended.

4. COMPUTATIONAL HARDWARE OVERVIEW

FIG. 11 is a block diagram that illustrates a computer system 1100 upon which an embodiment of the invention may be implemented. Computer system 1100 includes a communication mechanism such as a bus 1110 for passing information between other internal and external components of the computer system 1100. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit).). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1100, or a portion thereof, constitutes a means for performing one or more steps of one or more methods described herein.

A sequence of binary digits constitutes digital data that is used to represent a number or code for a character. A bus 1110 includes many parallel conductors of information so that information is transferred quickly among devices coupled to the bus 1110. One or more processors 1102 for processing information are coupled with the bus 1110. A processor 1102 performs a set of operations on information. The set of operations include bringing information in from the bus 1110 and placing information on the bus 1110. The set of operations also typically include comparing two or more units of information, shifting positions of units of information, and combining two or more units of information, such as by addition or multiplication. A sequence of operations to be executed by the processor 1102 constitutes computer instructions.

Computer system 1100 also includes a memory 1104 coupled to bus 1110. The memory 1104, such as a random access memory (RAM) or other dynamic storage device, stores information including computer instructions. Dynamic memory allows information stored therein to be changed by the computer system 1100. RAM allows a unit of information stored at a location called a memory address to be stored and retrieved independently of information at neighboring addresses. The memory 1104 is also used by the processor 1102 to store temporary values during execution of computer instructions. The computer system 1100 also includes a read only memory (ROM) 1106 or other static storage device coupled to the bus 1110 for storing static information, including instructions, that is not changed by the computer system 1100. Also coupled to bus 1110 is a non-volatile (persistent) storage device 1108, such as a magnetic disk or optical disk, for storing information, including instructions, that persists even when the computer system 1100 is turned off or otherwise loses power.

Information, including instructions, is provided to the bus 1110 for use by the processor from an external input device 1112, such as a keyboard containing alphanumeric keys operated by a human user, or a sensor. A sensor detects conditions in its vicinity and transforms those detections into signals compatible with the signals used to represent information in computer system 1100. Other external devices coupled to bus 1110, used primarily for interacting with humans, include a display device 1114, such as a cathode ray tube (CRT) or a liquid crystal display (LCD), for presenting images, and a pointing device 1116, such as a mouse or a trackball or cursor direction keys, for controlling a position of a small cursor image presented on the display 1114 and issuing commands associated with graphical elements presented on the display 1114.

In the illustrated embodiment, special purpose hardware, such as an application specific integrated circuit (IC) 1120, is coupled to bus 1110. The special purpose hardware is configured to perform operations not performed by processor 1102 quickly enough for special purposes. Examples of application specific ICs include graphics accelerator cards for generating images for display 1114, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1100 also includes one or more instances of a communications interface 1170 coupled to bus 1110. Communication interface 1170 provides a two-way communication coupling to a variety of external devices that operate with their own processors, such as printers, scanners and external disks. In general the coupling is with a network link 1178 that is connected to a local network 1180 to which a variety of external devices with their own processors are connected. For example, communication interface 1170 may be a parallel port or a serial port or a universal serial bus (USB) port on a personal computer. In some embodiments, communications interface 1170 is an integrated services digital network (ISDN) card or a digital subscriber line (DSL) card or a telephone modem that provides an information communication connection to a corresponding type of telephone line. In some embodiments, a communication interface 1170 is a cable modem that converts signals on bus 1110 into signals for a communication connection over a coaxial cable or into optical signals for a communication connection over a fiber optic cable. As another example, communications interface 1170 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1170 sends and receives electrical, acoustic or electromagnetic signals, including infrared and optical signals, which carry information streams, such as digital data.

The term computer-readable medium is used herein to refer to any medium that participates in providing information to processor 1102, including instructions for execution. Such a medium may take many forms, including, but not limited to, non-volatile media, volatile media and transmission media. Non-volatile media include, for example, optical or magnetic disks, such as storage device 1108. Volatile media include, for example, dynamic memory 1104. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1102, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1102, except for carrier waves and other signals.

Logic encoded in one or more tangible media includes one or both of processor instructions on a computer-readable storage media and special purpose hardware, such as ASIC 1120.

Network link 1178 typically provides information communication through one or more networks to other devices that use or process the information. For example, network link 1178 may provide a connection through local network 1180 to a host computer 1182 or to equipment 1184 operated by an Internet Service Provider (ISP). ISP equipment 1184 in turn provides data communication services through the public, world-wide packet-switching communication network of networks now commonly referred to as the Internet 1190. A computer called a server 1192 connected to the Internet provides a service in response to information received over the Internet. For example, server 1192 provides information representing video data for presentation at display 1114.

The invention is related to the use of computer system 1100 for implementing the techniques described herein. According to one embodiment of the invention, those techniques are performed by computer system 1100 in response to processor 1102 executing one or more sequences of one or more instructions contained in memory 1104. Such instructions, also called software and program code, may be read into memory 1104 from another computer-readable medium such as storage device 1108. Execution of the sequences of instructions contained in memory 1104 causes processor 1102 to perform the method steps described herein. In alternative embodiments, hardware, such as application specific integrated circuit 1120, may be used in place of or in combination with software to implement the invention. Thus, embodiments of the invention are not limited to any specific combination of hardware and software.

The signals transmitted over network link 1178 and other networks through communications interface 1170, carry information to and from computer system 1100. Computer system 1100 can send and receive information, including program code, through the networks 1180, 1190 among others, through network link 1178 and communications interface 1170. In an example using the Internet 1190, a server 1192 transmits program code for a particular application, requested by a message sent from computer 1100, through Internet 1190, ISP equipment 1184, local network 1180 and communications interface 1170. The received code may be executed by processor 1102 as it is received, or may be stored in storage device 1108 or other non-volatile storage for later execution, or both. In this manner, computer system 1100 may obtain application program code in the form of a signal on a carrier wave.

Various forms of computer readable media may be involved in carrying one or more sequence of instructions or data or both to processor 1102 for execution. For example, instructions and data may initially be carried on a magnetic disk of a remote computer such as host 1182. The remote computer loads the instructions and data into its dynamic memory and sends the instructions and data over a telephone line using a modem. A modem local to the computer system 1100 receives the instructions and data on a telephone line and uses an infra-red transmitter to convert the instructions and data to a signal on an infra-red a carrier wave serving as the network link 1178. An infrared detector serving as communications interface 1170 receives the instructions and data carried in the infrared signal and places information representing the instructions and data onto bus 1110. Bus 1110 carries the information to memory 1104 from which processor 1102 retrieves and executes the instructions using some of the data sent with the instructions. The instructions and data received in memory 1104 may optionally be stored on storage device 1108, either before or after execution by the processor 1102.

FIG. 12 illustrates a chip set 1200 upon which an embodiment of the invention may be implemented. Chip set 1200 is programmed to perform one or more steps of a method described herein and includes, for instance, the processor and memory components described with respect to FIG. 11 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 1200, or a portion thereof, constitutes a means for performing one or more steps of a method described herein.

In one embodiment, the chip set 1200 includes a communication mechanism such as a bus 1201 for passing information among the components of the chip set 1200. A processor 1203 has connectivity to the bus 1201 to execute instructions and process information stored in, for example, a memory 1205. The processor 1203 may include one or more processing cores with each core configured to perform independently. A multi-core processor enables multiprocessing within a single physical package. Examples of a multi-core processor include two, four, eight, or greater numbers of processing cores. Alternatively or in addition, the processor 1203 may include one or more microprocessors configured in tandem via the bus 1201 to enable independent execution of instructions, pipelining, and multithreading. The processor 1203 may also be accompanied with one or more specialized components to perform certain processing functions and tasks such as one or more digital signal processors (DSP) 1207, or one or more application-specific integrated circuits (ASIC) 1209. A DSP 1207 typically is configured to process real-world signals (e.g., sound) in real time independently of the processor 1203. Similarly, an ASIC 1209 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 1203 and accompanying components have connectivity to the memory 1205 via the bus 1201. The memory 1205 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 1205 also stores the data associated with or generated by the execution of one or more steps of the methods described herein.

5. ALTERATIONS, EXTENSIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article.

6. REFERENCES

All references cited herein are hereby incorporated by reference in their entirety. Asur, R., et al. 2015. High dose bystander effects in spatially fractionated radiation therapy. Cancer Lett; 356(1):52-7.

Buchsbaum, J. C. 2013. Proton therapy—What is it and what can it do to help my patients? Appl Rad Oncol; 2(1): 6-15.

Burnette, B. C., et al. 2011. The efficacy of radiotherapy relies upon induction of type i interferon-dependent innate and adaptive immunity. Cancer Res; 71:2488-96.

Dewan, M. Z., et al. 2009. Fractionated but not single dose radiotherapy induces an immune-mediated abscopal effect when combined with anti-CTLA-4 antibody. Clin Cancer Res; 15:5379-88.

Gao, M., et al. 2015, Spatially Fractionated (GRID) Radiation Therapy Using Proton Pencil Beam Scanning (PBS): A Feasibility Study. (abstract) Int J Radiat Biol Phys; 93(3):SE562.

Garcia-Barros, M., et al. 2003. Tumor response to radiotherapy regulated by endothelial cell apoptosis. Science; 300:1155-9.

Griffin, R. J., et al. 2012. Microbeam radiation therapy alters vascular architecture and tumor oxygenation and is enhanced by a galectin-1 targeted anti-angiogenic peptide. Radiat Res; 177:804-812.

Guan, F., et al. 2015. Spatial mapping of the biologic effectiveness of scanned particle beams: towards biologically optimized particle therapy. Sci Rep; 5:9850.

Haimovitz-Friedman, A., et al. 1994. Ionizing radiation acts on cellular membranes to generate ceramide and initiate apoptosis. J Exp Med; 180:525-35.

Haimovitz-Friedman, A., et al. 1994. Protein kinase C mediates basic fibroblast growth factor protection of endothelial cells against radiation-induced apoptosis. Cancer Res; 54:2591-7.

Henry, T., et al. 2016. Proton Grid Therapy. Technol Cancer Res Treat:1533034616681670.

Huhn, J. L., et al. 2006. Spatially fractionated GRID radiation treatment of advanced neck disease associated with head and neck cancer. Technol Cancer Res Treat; 5:607-612.

Ilnytskyy, Y., et al. 2009. Radiation-induced bystander effects in vivo are epigenetically regulated in a tissue-specific manner Environ Mol Mutagen; 50:105-13.

Kavanagh, B. D. Timmerman, R. D. 2006. Stereotactic radiosurgery and stereotactic body radiation therapy: an overview of technical considerations and clinical applications. Hematol Oncol Clin North Am; 20:87-95.

Khan, F. M. and Gibbons, J. P. 2014. Khan's the Physics of Radiation Therapy: Lippincott Williams & Wilkins.

Laissue, J. A., et al. Alban Kohler (1874-1947): inventor of grid therapy. Z. Med. Phys. 2012; 22:90-99.

Lee, Y., et al. 2009. Therapeutic effects of ablative radiation on local tumor require CD8+ T cells: changing strategies for cancer treatment. Blood; 114:589-95.

Lin, X., et al. 2000. Ceramide mediates radiation-induced death of endothelium. Crit Care Med; 28:N87-93.

Marks, H. 1952. Clinical experience with irradiation through a grid. Radiology; 58:338-342.

McMahon, S. J., et al. 2013. A kinetic-based model of radiation-induced intercellular signaling. PLoS One; 8:e54526.

Meyer, J., and Timmerman, R. 2011. Stereotactic ablative radiotherapy in the framework of classical radiobiology: response to Drs. Brown, Diehn, and Loo. Int J Radiat Oncol Biol Phys; 79:1599-600; author reply 1600.

Mohiuddin, M., et al., 1996. Spatially fractionated (GRID) radiation for palliative treatment of advanced cancer. Radia Oncol Invest, 4:41-47.

Mohiuddin, M., et al. 1999. High-dose spatially fractionated radiation (GRID): A new paradigm in the management of advanced cancer. Int J Radiat Oncol Biol Phys, 45:721-27.

Neuner G. A., et al. 2008. High-dose Spatially-fractionated GRID radiation therapy (SFGRT): A comparison of outcomes of treatment delivered through Cerrobend GRID versus MLC GRID. Int J Radiat Oncol Biol Phys, 72:5488.

Onishi, H., et al. 2004. Stereotactic hypofractionated high-dose irradiation for stage I nonsmall cell lung carcinoma: clinical outcomes in 245 subjects in a Japanese multiinstitutional study. Cancer; 101(7):1623-31.

Penagaricano, J. A., et al. 2010. Evaluation of spatially fractionated radiotherapy (GRID) and definitive chemo-radiotherapy with curative intent for locally advanced squamous cell carcinoma of the head and neck: initial response rates and toxicity. Int. J. Radiat. Oncol. Biol. Phys.; 76:1369-1375.

Santana, P., et al. 1996. Acid sphingomyelinase deficient human lymphoblasts and mice are defective in radiation-induced apoptosis. Cell; 86:189-99.

Sathishkumar, S., et al. 2002. The impact of TNF-alpha induction on therapeutic efficacy following high dose spatially fractionated (GRID) radiation. Technol Cancer Res Treat; 1:141-7.

Sathishkumar, S., et al. 2005. Elevated sphingomyelinase activity and ceramide concentration in serum of patients undergoing high dose spatially fractionated radiation treatment: implications for endothelial apoptosis. Cancer Biol Ther; 4:979-86.

Shareef, M. M., et al. 2007. Role of tumor necrosis factor alpha and TRAIL in high-dose radiation-induced bystander signaling in lung adenocarcinoma. Cancer Res; 67:11811-20.

Snider, J. W., et al. 2014. Use of "Virtual" High-Dose-Rate (HDR) Brachytherapy via Spatially Fractionated GRID Radiation Therapy (SFGRT) as Part of Neoadjuvant Therapy in Poor Prognosis, Bulky Sarcomas. Int J Radiat Oncol Biol Phys; 90(1):5767.

Snider, J, W., et al. 2017. A Novel Method for the Delivery of 3-Dimensional High-Dose Spatially Fractionated Radiation Therapy With Pencil Beam Scanning Proton Therapy: Maximizing the Benefit of the Bragg Peak. (abstract) Int J Radiat Oncol Biol Phys; 99(2):S232-3.

Videtic, G. M., et al. 2015. A Randomized Phase 2 Study Comparing 2 Stereotactic Body Radiation Therapy Schedules for Medically Inoperable Patients With Stage I Peripheral Non-Small Cell Lung Cancer: NRG Oncology RTOG 0915 (NCCTG N0927). Int J Radiat Oncol Biol Phys; 93(4):757-64.

Welsh, J. W., et al. 2017. Phase 2 5-Arm Trial of Ipilimumab Plus Lung or Liver Stereotactic Radiation for Patients with Advanced Malignancies. (abstract) Int J Radiat Oncol Biol Phys; 99(5):1315.

Wilson, R. R. Radiological use of fast protons. Radiology; 47:487-91.

Wu, X., et al, Method for three dimensional (3D) lattice radiotherapy. U.S. Pat. No. 8,395,131 B2 filing Jun. 20, 2010.

Wu, X., et al. On Modern Technical Approaches of Three-Dimensional High-Dose Lattice Radiotherapy (LRT). Cureus 2(3): e9.

Zhang, X., et al. 2016. Spatially fractionated radiotherapy (GRID) using helical tomotherapy. J Appl Clin Med Phys; 17(1):396-407.

Zwicker, R. D., et al. 2004. Therapeutic advantage of GRID irradiation for large single fractions. Int J Radiat Oncol Biol Phys, 58:1309-15.

What is claimed is:

1. A method for beam therapy comprising:
receiving first data indicating a target region inside a subject for particle therapy, a minimum dose inside the target region, and a maximum dose inside the subject but outside the target region;
determining a plurality of beam axis angles, each beam axis angle comprising a gantry angle and a couch position;
determining a plurality of spots within the target region;
determining for each beam axis angle a pristine beamlet with a corresponding scan beam angle and particle initial energy to direct a Bragg Peak at a spot of the plurality of spots;
repeating the determining the pristine beamlet step until every spot of the plurality of spots is subjected to a Bragg peak or an intersection of two or more of the pristine beamlets;
storing output data indicating the pristine beamlets; and
configuring automatic operation of a particle beam therapy apparatus based on said stored output data indicating the pristine beamlets;
wherein a spacing of the plurality of spots are based at least in part on a target spacing distance for a type of tissue in the target region.

2. The method of claim 1, wherein:
the method further comprises
determining, on a processor, a spatial distribution of a delivered dose inside the subject accumulated from the determined pristine beamlets at all of the plurality of beam axis angles, and
determining on the processor whether the spatial distribution of the delivered dose satisfies the first data; wherein
causing output data to be stored further comprises causing output data to be stored based on the determination that the spatial distribution of the delivered dose satisfies the first data.

3. The method of claim 2, wherein a portion inside a target region of the spatial distribution of the delivered dose is heterogeneous with a maximum and minimum in the delivered dose which differ by a factor in a range from 2 to 8.

4. The method of claim 3, wherein the minimum dose inside the target region is about 10 gray (Gy).

5. The method of claim 1, wherein the plurality of spots are spaced apart from each other by the target spacing distance.

6. The method of claim 1, wherein the plurality of spots are spaced apart from an edge of the target region by about the target spacing distance.

7. The method of claim 1, wherein the target spacing distance is in a range from 1 centimeter (cm) to 3 cm.

8. The method of claim 1, wherein determining the plurality of spots within the target region further comprises determining a grid of spots rotated relative to each beam axis angle such that each spot is separated in a beam's eye view for the beam axis angle by at least a sparing distance.

9. The method of claim 8, wherein determining for each beam axis angle the pristine beamlet further comprises determining a scan beam, having the corresponding scan beam angle and particle initial energy, for every spot in the beam's eye view for the beam axis angle.

10. A method for beam therapy comprising:
receiving first data indicating a target region inside a subject for particle therapy, a minimum dose inside the target region, and a maximum dose inside the subject but outside the target region;
determining a plurality of beam axis angles, each beam axis angle comprising a gantry angle and a couch position;
determining a plurality of spots within the target region;
determining for each beam axis angle two or more pristine beamlets, each beamlet having a corresponding scan beam angle and particle initial energy to direct a Bragg Peak at a spot of the plurality of spots;
repeating the determining the pristine beamlet step until every spot of the plurality of spots is subjected to a Bragg peak or an intersection of two or more of the pristine beamlets;
storing output data indicating the pristine beamlets; and
configuring automatic operation of a particle beam therapy apparatus based on said stored output data indicating the pristine beamlets;
wherein no two pristine beamlets determined for each beam axis angle are closer, inside the subject but outside the target region, than a scan separation distance based at least in part on a sparing distance.

11. The method of claim 10, wherein the scan separation distance is at least twice the sparing distance.

12. The method of claim 10, wherein the sparing distance is in a range from 1 centimeter to 3 cm.

13. A method for beam therapy comprising:
receiving first data indicating a target region inside a subject for particle therapy, a minimum dose inside the target region, and a maximum dose inside the subject but outside the target region;
determining a plurality of beam axis angles, each beam axis angle comprising a gantry angle and a couch position;
determining a plurality of spots within the target region;
determining for each beam axis angle a pristine beamlet with a corresponding scan beam angle and particle initial energy to direct a Bragg Peak at a spot of the plurality of spots, further comprising determining a scan beam, having the corresponding scan beam angle and particle initial energy, for every spot separated by at least a sparing distance in a beam's eye view for the beam axis angle;
repeating the determining the pristine beamlet step until every spot of the plurality of spots is subjected to a Bragg peak or an intersection of two or more of the pristine beamlets;
storing output data indicating the pristine beamlets; and
configuring automatic operation of a particle beam therapy apparatus based on said stored output data indicating the pristine beamlets;
wherein determining the plurality of spots within the target region further comprises determining the plurality of spots within the target region such that no two spots are coaxial in the beam's eye view along any of the plurality of beam axis angles.

14. The method of claim 13, wherein determining the plurality of spots within the target region further comprises determining a grid of spots separated by a distance based at least in part on a target spacing distance, wherein the grid is rotated such that each spot is separated in the beam's eye view for the beam axis angle.

15. A non-transitory computer-readable medium carrying one or more sequences of instructions, wherein execution of the one or more sequences of instructions by one or more processors causes the one or more processors to:
receive first data indicating a target region inside a subject for particle therapy, a minimum dose inside the target region, and a maximum dose inside the subject but outside the target region;
determine a plurality of beam axis angles, each beam axis angle comprising a gantry angle and a couch position;
determine a plurality of spots within the target region;

determine for each beam axis angle a pristine beamlet with a corresponding scan beam angle and particle initial energy to direct a Bragg Peak at a spot of the plurality of spots;

repeat the determination of the pristine beamlet step until every spot of the plurality of spots is subjected to a Bragg peak or an intersection of two or more of the pristine beamlets;

store output data indicating the pristine beamlets; and configure automatic operation of a particle beam therapy apparatus based on said stored output data indicating the pristine beamlets;

wherein a spacing of the plurality of spots is based at least in part on a target spacing distance for a type of tissue in the target region.

16. A system comprising:

a particle beam therapy apparatus;

at least one processor; and at least one memory including one or more sequences of instructions, the at least one memory and the one or more sequences of instructions configured to, with the at least one processor, cause the system to perform at least:

receiving first data indicating a target region inside a subject for particle therapy, a minimum dose inside the target region, and a maximum dose inside the subject but outside the target region;

determining a plurality of beam axis angles, each beam axis angle comprising a gantry angle and a couch position;

determining a plurality of spots within the target region;

determining for each beam axis angle a pristine beamlet with a corresponding scan beam angle and particle initial energy to direct a Bragg Peak at a spot of the plurality of spots;

repeating the determining the pristine beamlet step until every spot of the plurality of spots is subjected to a Bragg peak or an intersection of two or more of the pristine beamlets; a storing output data indicating the pristine beamlets; and configuring automatic operation of the particle beam therapy apparatus based on said stored output data indicating the pristine beamlets;

wherein a spacing of the plurality of spots is based at least in part on a target spacing distance for a type of tissue in the target region.

17. A non-transitory computer-readable medium carrying one or more sequences of instructions, wherein execution of the one or more sequences of instructions by one or more processors causes the one or more processors to:

receive first data indicating a target region inside a subject for particle therapy, a minimum dose inside the target region, and a maximum dose inside the subject but outside the target region;

determine a plurality of beam axis angles, each beam axis angle comprising a gantry angle and a couch position;

determine a plurality of spots within the target region;

determine for each beam axis angle two or more pristine beamlets, each beamlet having a corresponding scan beam angle and particle initial energy to direct a Bragg Peak at a spot of the plurality of spots;

repeat the determination of the pristine beamlet step until every spot of the plurality of spots is subjected to a Bragg peak or an intersection of two or more of the pristine beamlets;

store output data indicating the pristine beamlets; and configure automatic operation of a particle beam therapy apparatus based on said stored output data indicating the pristine beamlets;

wherein no two pristine beamlets determined for each beam axis angle are closer, inside the subject but outside the target region, than a scan separation distance based at least in part on a sparing distance.

18. A system comprising:

a particle beam therapy apparatus;

at least one processor; and at least one memory including one or more sequences of instructions, the at least one memory and the one or more sequences of instructions configured to, with the at least one processor, cause the system to perform at least:

receiving first data indicating a target region inside a subject for particle therapy, a minimum dose inside the target region, and a maximum dose inside the subject but outside the target region;

determining a plurality of beam axis angles, each beam axis angle comprising a gantry angle and a couch position;

determining a plurality of spots within the target region;

determining for each beam axis angle two or more pristine beamlets, each beamlet having a corresponding scan beam angle and particle initial energy to direct a Bragg Peak at a spot of the plurality of spots;

repeating the determining the pristine beamlet step until every spot of the plurality of spots is subjected to a Bragg peak or an intersection of two or more of the pristine beamlets;

storing output data indicating the pristine beamlets; and configuring automatic operation of the particle beam therapy apparatus based on said stored output data indicating the pristine beamlets;

wherein no two pristine beamlets determined for each beam axis angle are closer, inside the subject but outside the target region, than a scan separation distance based at least in part on a sparing distance.

19. A non-transitory computer-readable medium carrying one or more sequences of instructions, wherein execution of the one or more sequences of instructions by one or more processors causes the one or more processors to:

receive first data indicating a target region inside a subject for particle therapy, a minimum dose inside the target region, and a maximum dose inside the subject but outside the target region;

determine a plurality of beam axis angles, each beam axis angle comprising a gantry angle and a couch position;

determine a plurality of spots within the target region;

determine for each beam axis angle a pristine beamlet with a corresponding scan beam angle and particle initial energy to direct a Bragg Peak at a spot of the plurality of spots, further including to determine a scan beam, having the corresponding scan beam angle and particle initial energy, for every spot separated by at least a sparing distance in a beam's eye view for the beam axis angle;

repeat the determination of the pristine beamlet step until every spot of the plurality of spots is subjected to a Bragg peak or an intersection of two or more of the pristine beamlets;

store output data indicating the pristine beamlets; and configure automatic operation of a particle beam therapy apparatus based on said stored data indicating the pristine beamlets;

wherein determining the plurality of spots within the target region further comprises determining the plurality of spots within the target region such that no two spots are coaxial in the beam's eye view along any of the plurality of beam axis angles.

20. A system comprising:
a particle beam therapy apparatus;
at least one processor; and
at least one memory including one or more sequences of instructions,
the at least one memory and the one or more sequences of instructions configured to, with the at least one processor, cause the system to perform at least:
receiving first data indicating a target region inside a subject for particle therapy, a minimum dose inside the target region, and a maximum dose inside the subject but outside the target region;
determining a plurality of beam axis angles, each beam axis angle comprising a gantry angle and a couch position;
determining a plurality of spots within the target region;
determining for each beam axis angle a pristine beamlet with a corresponding scan beam angle and particle initial energy to direct a Bragg Peak at a spot of the plurality of spots, further comprising determining a scan beam, having the corresponding scan beam angle and particle initial energy, for every spot separated by at least a sparing distance in a beam's eye view for the beam axis angle;
repeating the determining the pristine beamlet step until every spot of the plurality of spots is subjected to a Bragg peak or an intersection of two or more of the pristine beamlets;
storing output data indicating the pristine beamlets; and
configuring automatic operation of the particle beam therapy apparatus based on said stored output data indicating the pristine beamlets;
wherein determining the plurality of spots within the target region further comprises determining the plurality of spots within the target region such that no two spots are coaxial in the beam's eye view along any of the plurality of beam axis angles.

* * * * *